United States Patent [19]

Yang

[11] Patent Number: 5,563,069
[45] Date of Patent: Oct. 8, 1996

[54] EXTRACTIVE FERMENTATION USING CONVOLUTED FIBROUS BED BIOREACTOR

[75] Inventor: Shang-Tian Yang, Dublin, Ohio

[73] Assignee: The Ohio State University Research Foundation, Columbus, Ohio

[21] Appl. No.: 101,926

[22] Filed: Aug. 4, 1993

Related U.S. Application Data

[63] Continuation-in-part of Ser. No. 873,405, Apr. 24, 1992, abandoned.

[51] Int. Cl.⁶ ............................................. C12M 1/14
[52] U.S. Cl. .................... 435/295.3; 435/297.1; 435/299.1
[58] Field of Search ........................ 435/174, 176, 435/177–180, 240.23, 283–286, 288, 310, 813, 299, 289.1, 293.1, 295.1, 295.2, 297.1, 297.2, 299.1, 295.3; 210/615, 150

[56] References Cited

U.S. PATENT DOCUMENTS

| 3,113,102 | 12/1963 | Schulze | 210/150 |
|---|---|---|---|
| 3,402,103 | 9/1968 | Amberg et al. | 210/615 |
| 3,617,541 | 11/1971 | Pan | 210/615 |
| 4,165,281 | 8/1979 | Kuriyama et al. | 210/150 |
| 4,546,083 | 10/1985 | Meyers et al. | 435/284 |
| 5,270,207 | 12/1993 | Matsumura et al. | 435/813 |
| 5,376,548 | 12/1994 | Matsuo et al. | 435/284 |

FOREIGN PATENT DOCUMENTS

| 2547574 | 12/1984 | France | 210/615 |
|---|---|---|---|
| 2565223 | 12/1985 | France | 210/615 |
| 2702043 | 7/1977 | Germany | 210/150 |
| 0125359 | 11/1978 | Japan | 210/615 |
| 0019584 | 2/1984 | Japan | 210/615 |
| 1034496 | 2/1989 | Japan | 210/615 |
| 2052094 | 2/1990 | Japan | 210/150 |
| 3178394 | 8/1991 | Japan | 210/150 |
| 0937597 | 9/1963 | United Kingdom | 210/150 |
| 2178477 | 2/1987 | United Kingdom | 435/285 |

| 9100339 | 1/1991 | WIPO | 435/314 |

OTHER PUBLICATIONS

Lewis et al. "Continuous Propionic Acid Fermentation . . . " Biotech and Bioeng. vol. 40 (1992) pp. 465–474.
Yang "A Novel Method to Produce Road Deicer from Cheese Whey", Proceeding of Waste Stream Minimization and Utilization (Apr. 1991) pp. 9.1–9.13.
Yang et al., "Extraction of Carboxylic Acis with Tertiary and Quaternary Amines: Effect of pH", *Ind. Eng. Chem. Res.*, 30, 1991, 1335–1342.

(List continued on next page.)

*Primary Examiner*—William Beisner
*Attorney, Agent, or Firm*—Kremblas, Foster, Millard & Pollick

[57] ABSTRACT

Apparatus and method for converting organic materials such as sugars and acids into other organic materials such as organic acids and salts other than the starting materials with immobilized cells. The invention is applicable to the conversion of the lactose content of whey, whey permeate or other lactose containing solutions and wastes into lactic acid, propionic acid, acetic acid, and their salts. The fermentation cells may be homolactic, homoacetic and propionic bacteria. The cells are immobilized onto the surface of and within convoluted sheets of a fibrous support material and reactant bearing fluids are caused to flow between the opposing surfaces of such convoluted sheets. Lactose containing solutions such as whey and whey permeate may be co-fermented with homolactic and homoacetic bacteria to acetic acid or acetate. The product may be extracted from its aqueous media by high distribution coefficient solvents particularly trioctylphosphine oxide and long-chain aliphatic secondary, tertiary and quaternary amines. The process and apparatus are particularly amenable to the economical production of calcium magnesium acetate and potassium acetate, which are useful as road deicing and anti-icing agents. The process and apparatus are also amenable to the economical production of calcium propionate and sodium lactate, which are useful as food preservatives.

18 Claims, 12 Drawing Sheets

OTHER PUBLICATIONS

Tang et al., "Acetic Acid Production from Whey Lactose by the co–Culture of Streptococcus Lactis and Clostridium Formicoaceticum", *Appl. Microbiol Biotechnol, 28, 1988 138–143*.

Yang et al., "Kinetics and Mathematical Modeling of Homoacetic Fermentation of Lactate by Clostridium Formicoaceticum", *Biotechnol. Bioeng.,* vol. 32, 1988, pp. 797–802.

Yang et al., "Kinetics of Homoacetic Fermentation of Lactate by Clostridium Formicoaceticum", *Appl Environ Microbiol, vol. 53, No. 4 1987, pp. 823–827*.

Hsu et al., "Propionic Acid Fermentation of Lactose by Propionibacterium acidipropionici: Effects of pH", *Biotechnol Bioeng, 38, 1991, 571–578*.

"Proceedings of Waste Stream Minimizaton and Utilization Innovative Concepts–An Experimental Technology Exchange", vol. 2, Washington, D.C., Apr. 25–26, 1991, U.S. Dept. of Energy.

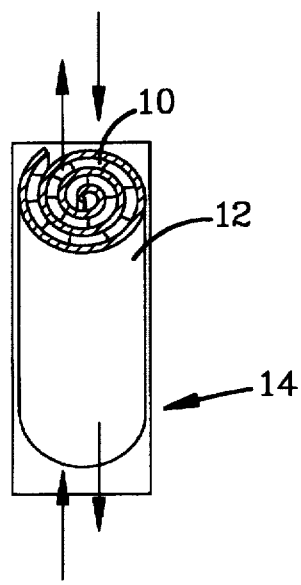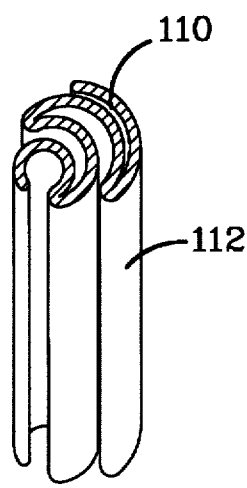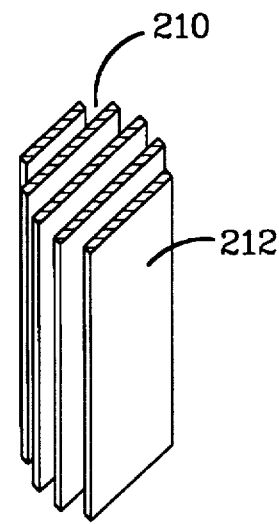
FIG-1A     FIG-1B     FIG-1C
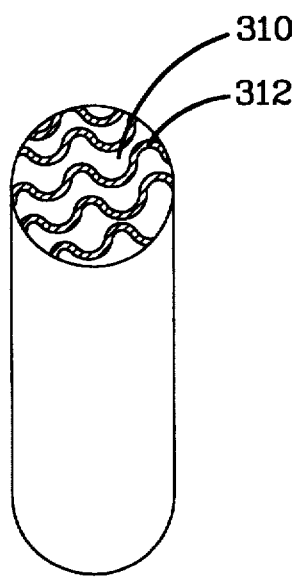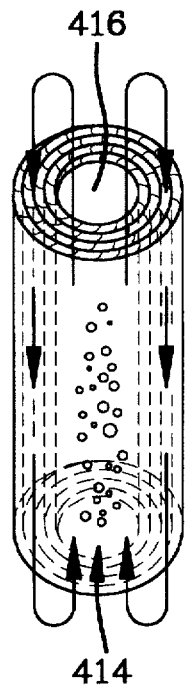
FIG-1D     FIG-1E 5,563,069

EXTRACTIVE FERMENTATION USING CONVOLUTED FIBROUS BED BIOREACTOR

This patent application is a continuation-in-part of patent application Ser. No. 07/873,405 filed Apr. 24, 1992, now abandoned.

FIELD OF THE INVENTION

This invention is a device and method for the conversion of organic materials to other organic materials and particularly for the conversion of sugars into organic acids and organic salts.

BACKGROUND OF THE INVENTION

Bio-processing is important in chemicals and drugs production. In many cases, when conventional chemical syntheses are not feasible or economical, bioprocessing is the only option for use. In general, bio-processes require gentler processing conditions and pose lesser environmental pollution problems than chemical processes do. However, a bioprocess usually has slower reaction rates than its chemical counterpart, and thus is often not chosen for use due to economic considerations.

The bioreactor is the center-piece of a bioprocess. The conventional bioreactors are derived from the reactors originally designed for homogeneous, chemical reactions. Most of industrial bioreactors in use today are not designed or operated optimally for multiphase, heterogeneous bio-reactions. Some major reasons that most bioprocesses have low reaction rates include the low (active) cell density in the bioreactor and the strong inhibition caused by the reaction products.

Cell immobilization in a bioreactor has long proved to be an effective method to improve reactor productivity of fermentation processes. It facilitates the separation of cells from products in solution and allows reactor operation at high dilution rates without cell washout. However, there are some major problems associated with conventional immobilized cell bioreactors that have prevented their wide industrial applications.

In general, cell immobilization is achieved either by cell entrapment within a confined volume through the use of a polymeric matrix or membrane, or by cell attachment via adsorption or covalent binding to a fixed surface, such as in a biofilm reactor. In conventional cell entrapment systems, overgrowth of cell biomass often causes serious problems during long-term operation of the bioreactor. Diffusion limitations and accumulation of dead cells over time result in loss of cell viability and thus reactor productivity. Also, conventional cell entrapment systems are not suitable for bio-processes which produce or use gases.

For a non-growing, immobilized cell system, the loss of cell viability and thus reactor productivity over time severely limits the operating life of the bioreactor. For an actively growing system, complications in maintaining bioreactor stability make continuous operation of the bioreactor rather difficult at industrial scale. For example, packed-bed and membrane, including hollow-fiber, bioreactors tend to get clogged quickly by cell biomass and fluidized-bed bioreactors are subject to unstable bed expansion due to biofilm growth. Conventional packedbed and membrane bioreactors also suffer from high pressure drop and gas entrapment inside the reactor bed that reduce the reactor working volume substantially. Nutrients transport in these immobilized cell systems also may become a problem due to diffusion limitations. Furthermore, conventional packed-bed and membrane bioreactors tend to accumulate aged or dead cells and gradually lose their production capability over time.

Product inhibition is another major factor in limiting bioprocess productivity. The product from a fermentation process usually is also an inhibitor to the cells used in the process. The removal of the fermentation product from the bioreactor thus can alleviate the product inhibition problem and improve reactor productivity by severalfold. In operation, the process integrates the downstream separation process with the fermentation, and is referred to as extractive fermentation. The extractive fermentation not only improves bioreactor productivity, it also makes the downstream product purification easier. Also, in some cases, extractive fermentation gives higher product yields than the conventional processes. An extractive fermentation involves the use of a second phase which is immiscible with the aqueous phase (fermentation broth), where bioreactions occurs, to continuously remove the product from the aqueous phase. The second phase used can be an organic solvent, polymeric aqueous solution, or a gas.

A packed-bed, immobilized cell structure has now been developed that overcomes the aforementioned problems. This bioreactor has been successfully used in long-term continuous fermentations for biochemicals production. In this new bioreactor, cells are immobilized within a convoluted fibrous matrix packed in a container. The convoluted fibrous structure is illustrated in FIG. 1. In this structure, the fibrous matrix provides large surface areas for cell attachment and a large void space for cell entrapment. Mass transfer limitations within the fibrous matrix can be controlled by using a proper thickness of the matrix layer. Growth of cells to a high density (40–100 g/L) thus can occur within the fibrous matrix. Also, the built-in vertical gaps among the spiral-wound layers of the fibrous matrix allow excess cell biomass to fall off to the bottom of the reactor, gases such as $CO_2$ and air to flow upward freely and escape from the top of the reactor, and the liquid medium to be pumped through the reactor bed without substantial pressure drop. Furthermore, the binding (adsorption) of cells to fiber surfaces can be regulated by the surface properties of the fiber. For example, loose cell attachments to hydrophilic fiber surfaces (such as cotton) would provide renewable surfaces for new cells and prevent aging or degeneration problems. The fibrous matrix functions as filter media and helps to retain cells (but not permanently) in the bioreactor. There is continual growth of new cells and sloughing-off of aged cells in the reactor. Therefore, the bioreactor is able to operate continuously for long periods without observable loss in its productivity. These operating advantages cannot be easily realized using conventional immobilized cell systems.

The new bioreactor can be effectively used in both aerobic and anaerobic processes. It also can be operated either as liquid-continuous or gas-continuous (trickle bed). In the trickle bed configuration, the gas (air) stream flows upward mainly through the spaces between the spiral matrix layers, while the liquid (water) stream flows downward through the fibrous matrix. The highly porous fibrous matrix provides high specific surface areas for cell attachment and for gas-liquid-solid contacts. Also, the large void space (>90%) within the fibrous matrix allows a large reactor working (liquid) volume for cell growth and reactions to take place. The fibrous bioreactor also can be used in extractive fermentation. The medium phase will be passed through the fibrous matrix, while the extractant phase through the gap between fiber layers. This novel bioreactor thus is versatile for use in various bioprocesses with multiphase flows and will find important applications in fermentation, biotransformation and biofiltration.

This new bioreactor has been tested in laboratory studies for several fermentation and extractive fermentation processes, including ethanol and recombinant protein production with yeasts, and organic acids (lactate, acetate and propionate) production with bacterial cultures. In all cases, superior reactor performance (e.g., three to tenfold increases in productivity and up to 1 year stable continuous operation) was obtained. It is reasonable to anticipate that this new bioreactor also will have advantageous applications in other bioprocesses such as in waste water treatment, biofiltration, biotransformation, and cell cultures.

Recently, extractive recovery of carboxylic acids from dilute, aqueous solutions such as fermentation broth and wastewater, which have acid concentrations lower than 10% (wt/wt), has received increasing attention. The extraction of organic acids using long-chain, aliphatic amines is especially important to the recovery and purification of organic acids or their salts from fermentation broth. For example, the acetate produced from a homoacetogenic fermentation is a strong inhibitor to the homoacetogen. Consequently, the fermentation rate would decrease dramatically as acetate is being produced. Also, the acetate concentration in the fermentation broth rarely reaches 4% (wt/vol) to allow economical recovery of acetate using conventional solvent extraction or distillation methods. A new two-step extractive separation of organic acids, such as acetate, by using aliphatic amines is developed (see FIG. 2) to overcome these problems. In this two-step extraction, the organic acid, such as acetic acid, present in the broth is first extracted with the extractant, such as Alamine 336, under acidic conditions. The extractant containing the organic acid is then backwashed or stripped with a concentrated alkaline solution to regenerate the extractant and to form the organic salt in concentrated solution simultaneously. The result is a concentrated organic salt solution that can be further concentrated or dried directly to form the final product. This method significantly cuts the energy costs in recovering and purifying organic acids or salts from dilute aqueous solutions. Also, an extractive fermentation which integrates the fermentation and extraction, as shown in FIG. 2, can be used to remove the fermentation product, such as acetic acid, from the bioreactor during fermentation and thus to reduce product inhibition and to enhance reactor productivity.

A particularly advantageous application of the structure and method of the present invention has been found in the conversion of fermentable sugars into organic acids and the salts of such acids. For example, lactose may be converted to lactic acid, acetic acid, propionic acid or the salts of these organic acids with appropriate fermentation cultures. All such conversions may be effected by known culturing means, however the use of the apparatus and method of the present invention substantially enhances the effectiveness of such conversions. Applications of the present inventions to convert the lactose content of whey into commercially useful calcium magnesium acetate, potassium acetate, calcium propionate, and sodium lactate have been found to be particularly advantageous.

Whey is a byproduct from the manufacture of cheese and casein. It contains about 5% lactose, 1% protein, 1% salts, and 0.1–0.8% lactic acid. The BOD (biological oxygen demand) content of whey is high—40,000 mg/L. The annual production of cheese whey in the United States has continuously increased to about 57 billion pounds (26 million metric tons) in 1988. Currently, only about 50% of the whey produced in the United States is used in human food and animal feed. The rest must find a new use or be treated as pollutant because of the high BOD content of whey. With continuous increases in milk and cheese production in the United States and throughout the world, the disposal of surplus cheese whey is one of the most critical problems facing the dairy industry.

While whey protein generally can be recovered from whey via ultrafiltration, the remaining lactose stream (whey permeate) represents a major disposal problem. Lactose accounts for 70%–80% of total whey solids. It can be readily isolated and purified from whey permeate by crystallization. However, the U.S. and world markets for lactose are cyclical and often very competitive. The market prices for lactose have fluctuated between $0.10/lb and $0.40/lb in the recent past. Furthermore, the lactose recovery yield from whey permeate is low (only about 60%), and the waste stream (commonly called mother liquor or de-lactosed whey permeate) from the crystallization process contains high salts (>20%), high lactose (~20%) and high BOD. Because of the high salt content, this mother liquor has limited applications and generally requires costly disposal. The increasing disposal costs have prompted continuous searches for better uses of whey, whey permeate, and de-lactosed whey permeate.

The utilization of whey lactose as a fermentation feedstock has been of great interest to the dairy industry. A wide range of products can be obtained from whey fermentations, including single cell protein, methane, alcohols (ethanol, butanol), organic acids (lactic, acetic, propionic, citric), vitamins, and biopolymers (xanthan gum etc.). However, production of a suitable fermentation product from whey must take into account technological, market, and economic factors. None of the existing whey fermentation processes have achieved wide-scale use in the dairy industry.

Most organic acids are presently produced via petrochemical routes due to the poor reaction rate found in conventional fermentation methods. Some organic acids, such as lactic, acetic, and propionic acids, and their salts, however, may be produced economically from fermentations of sugars (e.g., lactose, glucose, fructose, sucrose) and organic acids (e.g., lactate, pyruvate) present in culture media or biomass (e.g., whey, corn steep liquor, sulfite liquor).

Lactic acid is an important specialty chemical with a current market of about 40 million lbs per year in the U.S. It is currently used both as a food additive and as an industrial chemical. Lactic acid is produced either synthetically or biologically. The synthetic product is preferred in some industrial applications because of its high purity. However, fermentation can produce the pure L(+)- or D(−)-isomer or a mixture of the two, depending on the bacterium used. Such specific lactic acid isomers are important to the production of biodegradable lactic acid polymers which may replace polyesters and other non-biodegradable plastics in many applications. Thus, pure (polymer grade) lactic acid may become a commodity chemical in the near future. Commercial interests in lactic acid fermentation are high. Recently, several new lactic acid fermentation plants have been or are being constructed in the U.S., including two whey-based fermentation plants.

Propionic acid is an important chemical used in the production of cellulose plastics, herbicides, and perfumes. Propionic acid is also an important mold inhibitor. Its calcium, sodium, and potassium salts are widely used as food and feed preservatives. Presently, commercial production of propionic acid is predominantly by petrochemical routes. However, interests in producing propionic acid and calcium propionate from whey lactose and other cheap biomass using propionibacteria are high.

Acetic acid is an important rnw material in the chemical industry. The production of acetic acid in the U.S. was ~3.2 billion pounds in 1992. One major new use for acetic acid is in roadway deicing, where calcium magnesium acetate (CMA), produced from glacial acetic acid and dolomitic lime, is used as a deicer to replace road salt. Another similar new use for acetic acid is to use potassium acetate to replace urea and glycols in airport runways deicing. At the present time, commercial production of glacial acetic acid is exclusively by the petrochemical route. However, there has been high interest in producing acetic acid and acetate from fermentations of various biomass, including whey.

One of the incentives for producing inexpensive acetic acid or acetate is the interest in calcium magnesium acetate (CMA) for use as a substitute for road or highway deicing salt. Salt and chemical deicers continue to be the major way to control snow and ice on highways. From 10 to 14 million tons of road salt are used annually in the United States and Canada. Salt is an extremely effective snow and ice control agent and is very cheap. However, extensive use of rock salt (sodium chloride) as a deicing chemical has resulted in millions of dollars of loss each year due to its damage to highways and motor vehicles. Salt is extremely corrosive to concrete and metals, which are an integral part of the nation's infrastructure. Salt also is harmful to vegetation and poses an environmental threat to groundwater quality in some regions. A recent study in New York State showed that while a ton of road salt costs only $30, it causes more than $1,400 in damage. The Federal Highway Administration has long recognized this problem and recently has identified calcium magnesium acetate (CMA) as one of the most promising alternative road deicers.

CMA is a mixture of calcium acetate and magnesium acetate, currently being manufactured by reacting glacial acetic acid with dolomitic lime (Ca/MgO) or limestone (Ca/MgCO$_3$). CMA has a deicing ability comparable to salt. In contrast to salt, CMA is noncorrosive to vehicles, not harmful to highway concrete, bridges and vegetation, and has no identified environmental concerns. However, the present cost for CMA is high—$650/ton versus $30/ton for salt. This makes it too expensive to use CMA even though all of the material cost due to CMA can be offset by the savings in other costs. For this reason, CMA is currently used only in limited areas where corrosion control is required and in environmentally sensitive areas to protect vegetation and ground water from salt poisoning. The use of CMA as a chemical deicer, however, will be widely accepted if the CMA production cost can be reduced to $300/ton ($0.15/lb) or less. About 75% of the production costs for the present commercial CMA deicer can be attributed to the glacial acetic acid, which costs at about $0.2/lb, used in its manufacturing. A low-cost CMA may be produced from whey lactose using the new device and method disclosed in this invention.

A new method has now been devised wherein sugar containing solutions, such as whey or its equivalent lactose containing solution, may be fermented with cells such as anaerobic homolactic and homoacetic bacteria in the new immobilized cell bioreactors to achieve a broth containing the desired products, such as acetic acid and acetate. The organic acids present in the broth may then be recovered and concentrated to form organic salts by using the two-step extraction method.

It is therefore the object of the invention to provide an effective apparatus and method for converting organic materials into more useful organic materials through fermentations.

It is also an object of the present invention to provide an improved way for converting sugars or sugar-containing biomass into organic acids, the salts of such acids and other biochemicals through the use of microorganisms.

A further object of the present invention is to provide a method and apparatus for converting lactose into useful organic acids or organic salts.

It is a further object of the invention to provide an apparatus and method for converting whey lactose (or its sugar or lactose containing equivalent) into useful organic acids or organic It is a further object of the invention to provide a method and apparatus for continuously converting whey lactose (or its sugar or lactose containing equivalent) into useful organic acids or organic salts.

Another object of the present invention is to provide a new, improved, immobilized cell bioreactor for uses in various bioprocesses, including fermentations, biotransformations, and biofiltrations, for the purpose of converting organic materials into something more desirable.

SUMMARY OF THE INVENTION

Organic materials, including fermentable sugars (such as lactose, glucose, galaclose, fructose, sucrose, etc.), starch, cellulose, organic acids and salts (such as lactate, pyruvate, succinate, etc.) are converted into other organic materials, including alcohols, organic acids, and organic salts, by exposure to cells known to be capable of effecting such conversions that have been immobilized in bioreactors containing a convoluted sheet or convoluted sheets of a fibrous supporting material. Such convolutions are disposed to allow a fluid (normally a liquid) containing such organic materials to flow between the adjacent convoluted surfaces of said supporting material so as to be in intimate contact with the adjacent cells immobilized on such surfaces.

Sugar solutions may be subject to fermentation with immobilized bacteria that will convert the sugar content into useful organic acid or salt under anaerobic conditions. The organic acid product is then extracted from the liquid media with solvents. Also, organic acids, such as lactic acid, may be converted to other organic acids or salts such as acetic acid or acetate by such fermentation. Propionic acid also can be fermented from lactate.

The sheet material utilized for immobilizing the living cells may be of any fibrous material on which living cells can be immobilized and which can be put in a convoluted form. Preferred materials are porous fibrous sheet materials such as cotton cloth, medical gauze, polyester fabrics, fiber glass mat and paper, etc. In such materials the living cells may be immobilized not only on the surface of the support but also within the porous structure increasing the surface area of contact between the living cells and the organic matter to be converted. The convolutions may be spiral or wound structures, folded sheet structures or sheet laminates or any other convolutions that will allow a fluid flow between the surfaces of such sheets (see FIG. 1). Although substantially parallel sheets are preferred to attain an even distribution within the container such parameter is not considered to be essential. The surfaces of such sheets are spaced to allow fluid flow therebetween. Such spacing must be sufficient to avoid a packed bed type structure with its disadvantages but sufficient to permit intimate contact of the bacteria immobilized on the opposing surfaces to achieve adequate contact with the reactants within the fluids flowing therebetween. Depending on the reaction conditions, an average gap between two such adjacent surfaces ranging from ~0.2 mm to as large as 20 mm may be adequate.

When soft fibrous materials, such as terry cloth, are use it in the convoluted structure, spacers may be used to keep two adjacent sheets apart or the fibrous sheets may be laminated with steel cloth to hold them in place. There are other means to maintain the convoluted structure. Although the convoluted fibrous structure is most likely to be used with a cylindrical column or tank as the bioreactor housing, it also can be used with rectangular or other geometric congers. The structure consisting of parallel sheets is thus also considered as one type of the convoluted structure.

When highly porous fibrous materials are used, the majority of cells in the bioreactor are present in the void space wig the fibrous matrix. High cell densities, as high as 100 g/L, can be achieved in such a fibrous bed bioreactor. Cells immobilized in this bioreactor are continuously renewed since new cells are replacing aged and dead cells. The aged cells and excess cell biomass are continuously sloughing off from the fibrous matrix. The bioreactor can be operated continuously without interruption for long period of time (several months to more than a year).

The structured fibrous bed is especially ideal for bioprocesses involving multiphase flow. For example, liquid and solid can flow through the gap between fibrous sheets as well as the void space within the porous fibrous layer, while gases can flow, mainly upward, through the gap between fibrous sheets. Also, a second liquid phase, immiscible to water, can flow through the gap while the aqueous phase flow through the fibrous matrix. In this case, the preferred fibrous material is a cotton cloth or other hydrophilic water absorbent so that cells will stay in the aqueous phase. Cells present in the fibrous matrix will be protected from contact damages by organic solvents, if used in extractive fermentation, and shear damages by gas bubbles, especially when air is sparging through the bioreactor. The device is thus also useful in cultivating cells and tissues sensitive to shear and bubble damages.

The bioreactor also may be operated as a trickle bed, where liquid (aqueous phase) is flowing down mainly through the porous fibrous matrix sheets and gases, usually air and carbon dioxide, occupy the gap between the fibrous sheets and flow upward. Another variation in the fibrous matrix packing structure is to have a hollow core, as shown in FIG. 1.e, and the bioreactor is operated as an air-lift reactor. In this design, air is sparged through the hollow core area and liquid is circulated through the fibrous matrix. These structures are particularly useful for aerobic bioprocesses. The trickle bed is also useful in extractive fermentation where a gas, such as carbon dioxide, is used to strip the fermentation product.

Packed bed, immobilized cell bioreactors, constructed in accordance with the present invention, were developed for the purpose of bioprocessing (such as fermentation). The microbial cells are immobilized on the fibrous matrix. Such matrix normally consists of fibrous sheets positioned in a container such as a bioreactor and convoluted so that there is adequate spacing between the convoluted surfaces to allow cell deposition and penetration of the reactants (i.e. sugars or organic acids) to pass through such structures. This packing design allows good contact between two different phases (gas-liquid or solvent-aqueous two phases) and is scaleable. Because the reactor bed is not completely filled with the solid matrix, the bioreactor can be operated for a long period without suffering from problems such as clogging and high pressure drop usually associated with conventional packed bed and membrane bioreactors.

Particularly useful conversions of whey lactose to acetic acid or acetate are achieved through the use of an immobilized coculture consisting of homolactic and homoacetic bacteria, such as *Streptococcus lactis* and *Clostridium formicoaceticum*, respectively. The two bacteria work together to convert lactose, the main component of whey, to lactate and then to acetate under anaerobic conditions. Other organic acids, including lactic acid and propionic acid, and their salts also can be produced from whey more efficiently through the use of the convoluted fibrous bed bioreactor. Other biochemicals, such as ethanol and proteins, also can be produced with the use of this bioreactor to improve their production efficiency. Similarly, the same bioreactor structure can be used in biofiltration and waste water treatment to improve their process efficiency.

Solvents with a high distribution coefficient can be used to extract organic acids or organic salts from a low concentration fermentation solution. These include trioctylphosphine oxide (TOPO) and long-chain aliphatic amines (including secondary, tertiary and quaternary amines). Quaternary amines, such as Aliquat 336, can extract both dissociated and undissociated carboxylic acids. TOPO and secondary and tertiary amines (much as Alamine 336) can only extract undissociated acids. These solvents can be used to separate the acid from fermentation broth, whose pH value must be below 7 (preferably at 4). Back-extraction with an alkaline solution (with pH above 10) then followed to regenerate the extractant and to form the organic salt in a concentrated solution. This two-step extraction method provides an energy-efficient way to recover and separate organic acids from dilute fermentation broth.

BRIEF DESCRIPTION OF THE DRAWINGS

FIGS. 1a to 1e are illustrative views of configurations of convoluted matrices for immobilized cells constructed in accordance with the present invention.

DETAILED DESCRIPTION OF THE INVENTION

Figure 2:
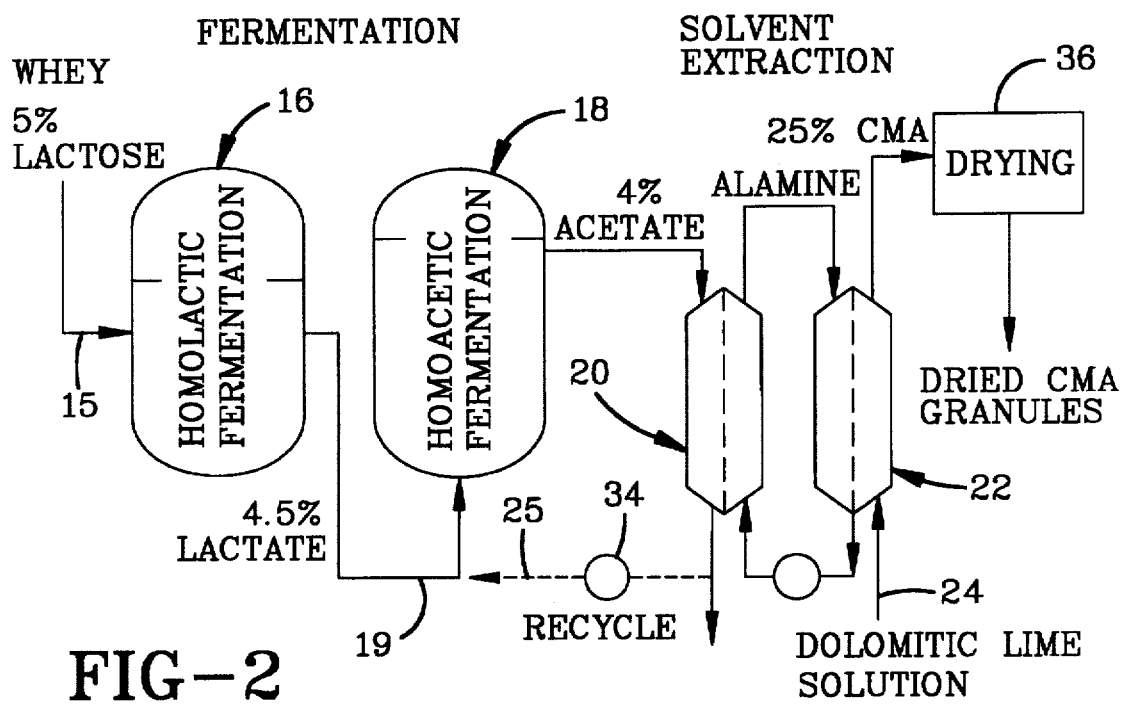
FIG. 2 is a schematic illustrative view of the extractive fermentation process for CMA production from whey.

FIG. 1a illustrates the convoluted structure, which consists of spiral wound fibrous sheet material (such as terry cloth) 12 and space 10 between two adjacent surfaces filled in the reactor 14. Cells are immobilized mainly on the surfaces of the fibers and within the void spaces of the fibrous matrix. The aqueous phase may flow through the spaces between two fiber surfaces and within the fibrous matrix, as well. A second phase (such as gas, solid, or a water-immiscible liquid), if present, flows mainly through the spaces between two adjacent surfaces. The flow direction for these two phases can be the same or in opposite as indicated by the arrows. FIGS. 1b, 1c and 1d illustrate several convoluted structures other than the strictly spiral structure of FIG. 1a which also may be employed as the immobilized cell structure utilized in accordance with the method of the present invention. In the structure of FIG; 1b the fibrous sheet material 112 is folded to fill the reactor (not shown) leaving space 110 between the surfaces of sheet material 112 for fluid flow. In the structure of FIG. 1c the matrix sheets 212 are parallel laminates filling the reactor (not shown) but spaced to provide space 210 for fluid flow. In the structure of FIG. 1d, corrugated sheet material 312 fills the reactor (not shown), leaving space 310 between the surfaces of the corrugated sheets for fluid flow. The structure of FIG. 1e consists of spiral windings of fibrous material 412 and a hollow core 416 to allow the reactor to operate as an air-lift bioreactor when air 414 is pumped through the hollow core area.

It will be appreciated that the exact convoluted structures of the fibrous sheet material are not critical so long as their adjacent surfaces allow fluid flow therebetween. Such structure could consist of a combination of laminated, folded and spiraled sheets or such structure may be of random contortions so long as such sheet surfaces extend substantially parallel to the direction of fluid flow and are spaced to effect opposing surfaces for fluid flow and immobilized cell-reactant contact. For the purposes of this application all such structures shall be within the meaning of the word "convoluted".

A continuous fermentation process using immobitlized cell bioreactors has been shown to generate less cell biomass and, thus, has lower nutrient requirements while maintaining high production rates and high product yields. Our fibrous bed bioreactor was shown to have a high cell density ranging from 30 g/L to 100 g/L, depending on the cultures and fermentation conditions used. Cell immobilization in the fibrous bioreactor is not irreversible since constant growth of new cells and sloughing off dead cells occurred within the reactor. The reactor is thus self-renewing and eventually establishes a dynamic steady-state cell population. Therefore, it is possible for the bioreactor to be operated for long periods of time. The bioreactors used in this work have been in continuous operation for over 6 months without encountering any contamination or degeneration problems.

No one bacterium or cell culture can efficiently convert whey (lactose) to acetate. However, acetate can be produced from whey permeate by using a co-culture consisting of homolactic (Streptococcus lactis) and homoacetic (Clostridium formicoaceticum) bacteria. These two bacteria work together to convert lactose, the main organic component of whey, to lactate and then to acetate under anaerobic conditions:

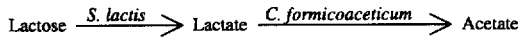

Lactose $\xrightarrow{S.\ lactis}$ Lactate $\xrightarrow{C.\ formicoaceticum}$ Acetate Using these two bacteria, acetate has been produced from both a lactose medium and whey permeate in laboratory batch fermentors when the pH was maintained at ~7 by continuous addition of NaOH or KOH. The acetate yield from lactose was >90%, and ~0.5M (or 3% wt/v) acetate concentration was attained.

The acetate yield from lactose in the present homofermentative process wherein the bacteria are immobilized is close to 100%. In contrast to the aerobic vinegar process, for which only 60% of the substrate carbon can be recovered as the acetic acid, the anaerobic process has a much higher yield and requires lower energy input for fermentation. Also, comparing with other anaerobic acetic fermentations, this co-cultured fermentation is the only effective way to produce acetate from lactose.

The preferred conditions for this co-cultured fermentation are 37° C. and pH 7.6. Although S. lactis and C. formicoaceticum have been found to be desirable fermentation bacteria for the transformation of the lactose of whey to acetic acid or acetate, other anaerobic homolactic and homoacetic bacteria also can be used for such purpose. Examples of such homolactic bacteria are Lactobacillus helveticus and L. bulgaricus. Acetobacterium woodii, A. carbinolicum and Acetogenium kivui are examples of other homoacetic bacteria that may be used. Other known microbial cultures and fermentation conditions may be substituted for this application.

Fermentatively produced acetic acid usually is recovered by solvent extraction and/or azeotropic dehydration. However, the acetic acid produced in the anaerobic fermentation at pH 7 is in the form of acetate salt. Conventional solvents can extract only free acid from the fermentation broth. Research has been conducted to overcome this problem by adapting the microbes to the acidic pH, or by acidifying the broth before extraction. However, neither of these two approaches could reduce the acetic acid recovery cost to an economically competitive level.

The highest concentration of acetic acid that most anaerobic homoacetogens can tolerate is lower than 3%. However, most extraction solvents require a concentration of acetic acid higher than 10% in order to have economical recovery of the acid product, and, therefore, an evaporation process is usually recommended prior to solvent extraction. Nevertheless, if a highly efficient extractant is available, the heating process can be reduced to a level sufficient only for killing the microbes in the liquor. Solvents with a high distribution coefficient can be used to extract carboxylic acids, such as acetic acid, from a low concentration solution. These include trioctylphosphine oxide (TOPO), and long-chain aliphatic (including secondary, tertiary and quaternary) mines. These extractants usually can only extract the undissociated acid in water, but quaternary amines such as Aliquat 336 also can extract the dissociated acid. In general, secondary (such as Adogen 283-D) and tertiary (such as Alamine 336) amines have better properties and are less expensive than TOPO and quaternary amines for use in extraction.

An extractive separation and recovery process normally involves two steps: extraction and solvent regeneration. Secondary and tertiary amines are only capable of extracting undissociated acid and thus will not extract organic acids under basic conditions. This characteristic allows solvent regeneration through back-extraction with an alkaline solution. Therefore, these amines can be easily regenerated by stripping with a small volume of an alkaline solution. The extraction of carboxylic acids with amines is thus highly energy-efficient, and will provide an economical method for recovering organic acids and their salts from dilute, aqueous solutions.

Extractive fermentation has the advantage of removing inhibitory products in situ, and can be used to control the reactor pH and to increase the fermentation rate for organic acid production. Previous studies have shown that the reactor productivity would be increased at least severalfold when the acid product is removed in situ by extraction. Also, the product from extractive fermentation is present in a relatively pure and concentrated form, and thus, saving in the downstream recovery and purification costs can be realized.

Successful operation of an extractive fermentation process requires careful selection of a non-toxic solvent for extraction. Most organic solvents are toxic to bacteria; they will either inhibit or stop bacterial growth. This solvent toxicity effect can be reduced or eliminated by minimizing the contact between cells and solvents, and by using solvents which are essentially insoluble in water. Cells present in the immobilized forms are protected from direct contact with the solvent, and thus are better than free, suspended cells. One tertiary amine (Alamine 336), which has an extremely low solubility in water and has proved not to be very toxic to several anaerobic bacteria used in organic acids fermentations, may be used for this purpose.

FIG. 2 shows a continuous, extractive fermentation process using immobilized cell bioreactors developed for CMA production from whey permeate. A continuous process using immobilized cell bioreactors will have the following advantages: higher reactor productivity, less cell mass formation and thus, lower nutrients requirement and higher product yields. The immobilized cell bioreactor is also less subjected to solvent toxicity imposed by the extractant used in an extractive fermentation process.

The bacterial cells are immobilized in a spiral wound, fibrous matrix 12 in the bioreactor 14 (FIG. 1a). The cells are immobilized in the spiral matrix by attachment to the fibrous surfaces and entrapment within the void volume of the fibrous matrix. The spiral structure is a flat sheet generally of a fibrous material such as terry cloth rolled vertically into a spiral, as shown by FIG. 1, leaving sufficient room between adjacent spiral surfaces to allow the reactant to pass through the structure and effect intimate contact with such cells.

The fermentation process of FIG. 2 involves two stages, the first stage for homolactic fermentation, effected in bioreactor 16 of FIG. 2 which corresponds structurally to reactor 14 of FIG. 1a, and the second stage for homoacetic fermentation, effected in bioreactor 18 of FIG. 2 which also corresponds to reactor 14 of FIG. 1a. This will allow the two different bacteria to grow at two different optimal conditions. However, depending on the final process design and economics, one-stage fermentation processes with both homolactic and homoacetic bacteria situated in the same bioreactor is also feasible.

Whey (or other lactose source) is introduced into bioreactor 16 as shown by the arrow 15 where it passes through immobilized cells (*S. tacas*) attached on and within a spiral structure such as shown by FIG. 1. The lactose content of the whey is converted to lactate or lactic acid. The effluent is then fed through line 19 into the reactor 18 where it flows upward through a spiral structure such as that shown by FIG. 1 but where the cells are the homoacetic bacterium *C. formicoaceticum* which converts the lactic acid or lactate to acetic acid or acetate.

The product yields in these two fermentations are ~98% and ~97%, respectively. Therefore, the overall acetate yield from lactose in this two-step fermentation is ~95%. About the same acetate yield would be obtained if both bacteria are co-immobilized in one bioreactor.

The second bioreactor 18, or homoacetic fermentation, is connected to extractor 20 represented in FIG. 2. The recycle line 28 and accompanying pumps 34 are optional devices that enhance the overall efficiency of the fermentation system. They integrate the fermentation with extraction and serve to continuously separate the fermentation product, acetic acid, form the bioreactor 18. Since the produced acetic acid is removed from the reactor 18, there is no need to add excessive mounts of alkali to maintain the pt. Thus, high fermentation rates can be attained.

Acetic acid present in the extractant is then stripped by back-extraction with a high-concentration alkaline (dolomitic lime or limestone) solution, as shown by the arrow 24, in the extractor 22 of FIG. 2. Thus, a concentrated acetate (CMA) stream is obtained and the extractant is regenerated simultaneously. Them is no need to further concentrate the CMA solution before drying. Also, there is no need for expensive distillation to regenerate the extractant. Since CMA, as a road deicer, needs not be as pure as acetic acid (as a chemical) and distillation is no longer needed, the recovery costs for CMA from this process will be low. The economics thus become favorable to the production of CMA from whey permeate. About 1.2 lb CMA can be produced from each lb of lactose fermented, at an estimated cost of $0.15/lb CMA or less.

Dryer 36 serves to provide CMA in a usable solid form. The drying step can be eliminated if a liquid product in concentrated solution is desired. Depending on the extractant used, some pH adjustment for the fermentation broth with acids, such as sulfuric acid, may be desirable for better extraction efficiency.

The process illustrated in FIG. 2 is only an example showing how an organic salt (CMA) may be produced from whey lactose using present invention. The process of the present invention is applicable to the conversion of any sugar and lactate to acetic acid or acetate. Although the present process is particularly useful in the treatment of whey it is applicable to any biomass source containing fermentable sugars, including glucose, fructose and sucrose, and lactate. Such biomass may consist of whey permeate, dextrose converted from grain sources, and lactate present in corn steep liquor. For the purpose of this invention all such whey equivalent solutions are included in the definition of "whey". The process of the present invention is also applicable to the conversion of sugars to other organic acids and organic salts such as propionic acid and lactic acid and their salts. These organic salts also can be produced from whey or other sugar-containing streams using similar processes with appropriate microbial cultures and alkali materials. Some examples of these organic salts are potassium acetate, calcium propionate, and sodium lactate.

Experimental

Homolactic acid bacteria, *Streptococcus lactis* (OSU stock culture #588) and *Lactobacillus helveticus* (ATCC 15009) were used in lactic acid production from lactose. *Clostridium formicoaceticum* (ATCC 27076) was used for homoacetic fermentation of lactate. For the co-cultured fermentation of whey lactose to acetate, *S. lactis* and *C. formicoaceticum* were used. *Propionibacterium acidipropionici* (ATCC 4875) was used for propionic acid fermentation. Stock cultures of these bacteria were maintained in synthetic media. The compositions of and preparation procedures of these media are well known and can be found in literature.

Sweet whey permeate, de-lactosed whey permeate, and acid whey were used in the following examples. Only the sweet whey permeate was membrane-sterilized by using a 0.2 μ-m (pore size) filter, while the other two whey materials were heat-sterilized and only their supernatants were used in feeding the bioreactor. Unless otherwise noted, no nutrient supplementation was used with these feed substrates.

Several batch fermentations were also conducted with 20-ml serum tubes and 2-liter agitated fermentors for comparison purposes and to screen for nutrient effects. When serum tubes were used, cell growth was followed by measuring the optical density of the tube using a spectrophotometer. When the fermentor was used, the headspace of the fermentor was pressurized with $N_2$ at 5 psig to maintain anaerobiosis in the fermentor. Following cell growth, 4-ml liquid samples were taken at various times. The cell concentration was determined by measuring the optical density. Liquid samples were then frozen and stored for future HPLC analysis.

The immobilized cell bioreactors used in this study were each made of a glass column (5 cm I.D.×45 cm) fired with a water jacket. The fibrous matrix used for cell immobilization was made from a piece of cotton towel (~5 mm thick) overlaid with a stainless steel cloth, spirally wound around the vertical axis with ~5 mm gap between two adjacent layers, and packed in the glass column. The packed fibrous matrix in the reactor had ~90% void volume. Depending on the packing volume used, the reactor working volume ranged from 270 mL to 450 mL.

Figure 3:
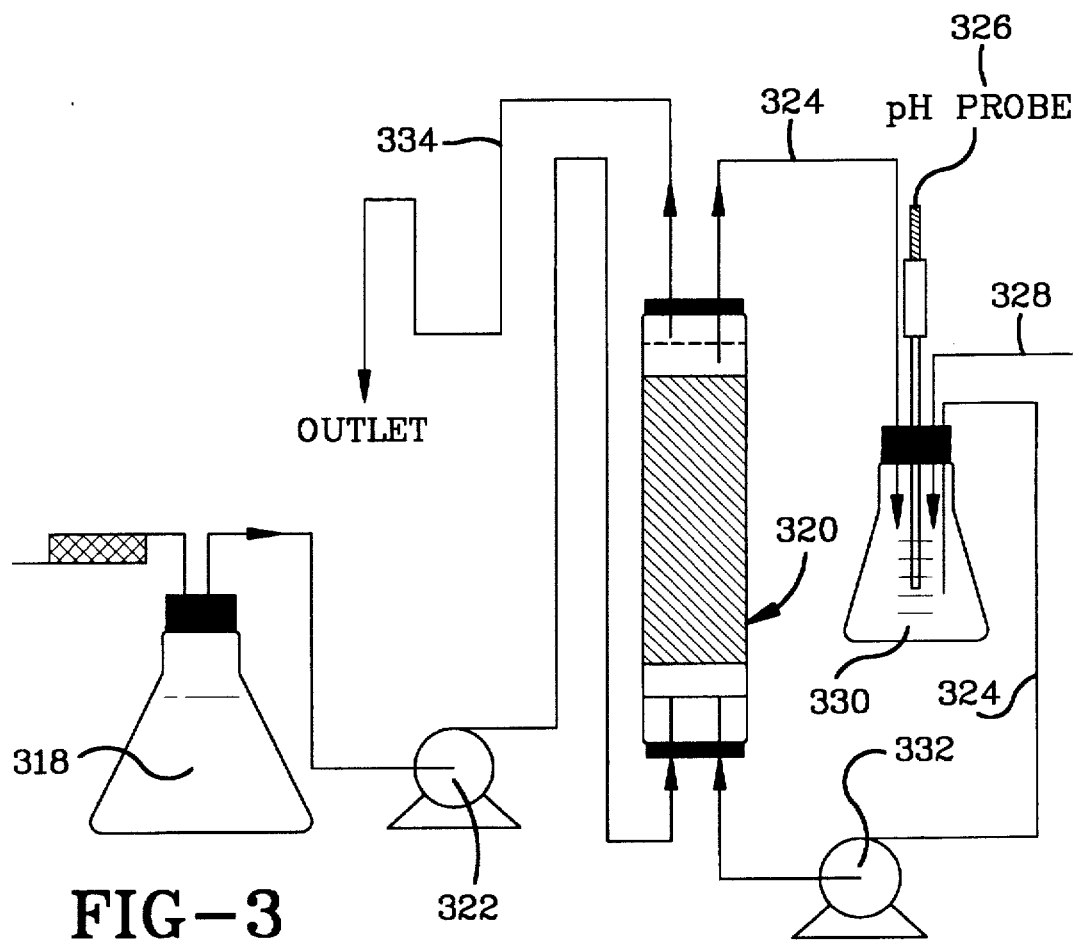
FIG. 3 shows a schematic diagram of the bioreactor system used in a study described hereafter.

FIG. 3 shows the schematic diagram of a typical bioreactor system used in experiments. The feed 318 was pumped into the reactor 320 by using a peristaltic pump 322 (Masterflex with #13 pump head, Cole-Parmer, Chicago, Ill. A recirculation stream 324 was also installed to provide mixing in the reactor. The bioreactor was maintained at a constant temperature by circulating constant-temperature water through the water jacket (not shown). A pH probe 326 was also installed in the container 330 in the recirculation loop, and the reactor pH was controlled at a desired value by using a pH controller to automatically add base to the reactor at 328. The base used in controlling the pH was one of the following: 6N NaOH solution, 6N KOH solution, 20% (wt/v) CaO suspension in water, or 20% MgO suspension in water.

Before start-up and operation each bioreaetor was autoclaved for 45 minutes twice, then filled with synthetic medium and inoculated with 40 ml cells. The cells in the bioreactor were allowed to grow for 2–3 days. Then, a synthetic medium was continuously fed into the bioreactor at a slow flow rate of ~150 mL/d for several days. The feed rate was gradually increased as the cell biomass in the bioreactor was built up. It took about 10 days for the new bioreactor packing to be saturated with cells and to reach steady state. The feed was then changed to whey permeate and fermentation kinetics and reactor performance at various feeding rates were studied. Unless otherwise noted, all kinetic studies were conducted under well-mixed (CSTR) conditions, with a recirculation rate of ~25 L/d.

The bioreactor performance was monitored by checking the optical density (OD) and acids content of the effluent from the reactor outlet. The actual feed rate was routinely checked by measuring the actual volume of the liquid medium collected at the reactor outlet over a known period of time. Once the reactor had reached a (pseudo-) steady state, liquid samples were collected and stored for future I-IPLC assays.

At the end of each reactor study, the cell density in the immobilized cell bioreactor was estimated by following procedures: first, all the liquid in the bioreactor was drained, and its volume and OD were measured. This information was used to estimate the total suspended cells (cells in the free solution) present in the reactor. Then, the drained fibrous matrix was removed from the reactor and washed several times until almost all cells have been removed, as indicated by the washing water being almost clear. The total volume of the washing water and its OD was then measured and used to estimate the total amount of cells immobilized in the fibrous matrix.

Cell concentration in solution was monitored by measuring the optical density at 660 nm ($OD_{660}$) using a spectrophotometer. Lactose, pyruvic, succinic, lactic, propionic, and acetic acids in the sample solution were analyzed with high performance liquid chromatography (HPLC).

EXAMPLE 1

Homolactic Acid Fermentations

Figure 4A:
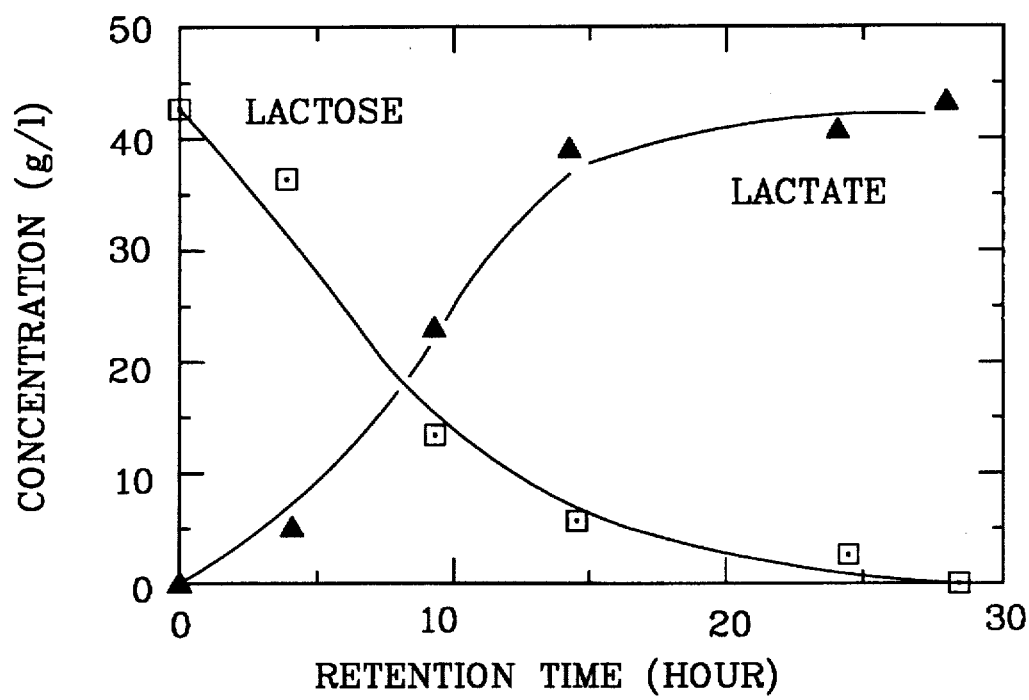
FIGS. 4a and 4b are graphs showing the homolactic fermentation with *S. lactis* for lactate production from lactose and whey permeate, respectively, using the method of the present invention.
Figure 4B:
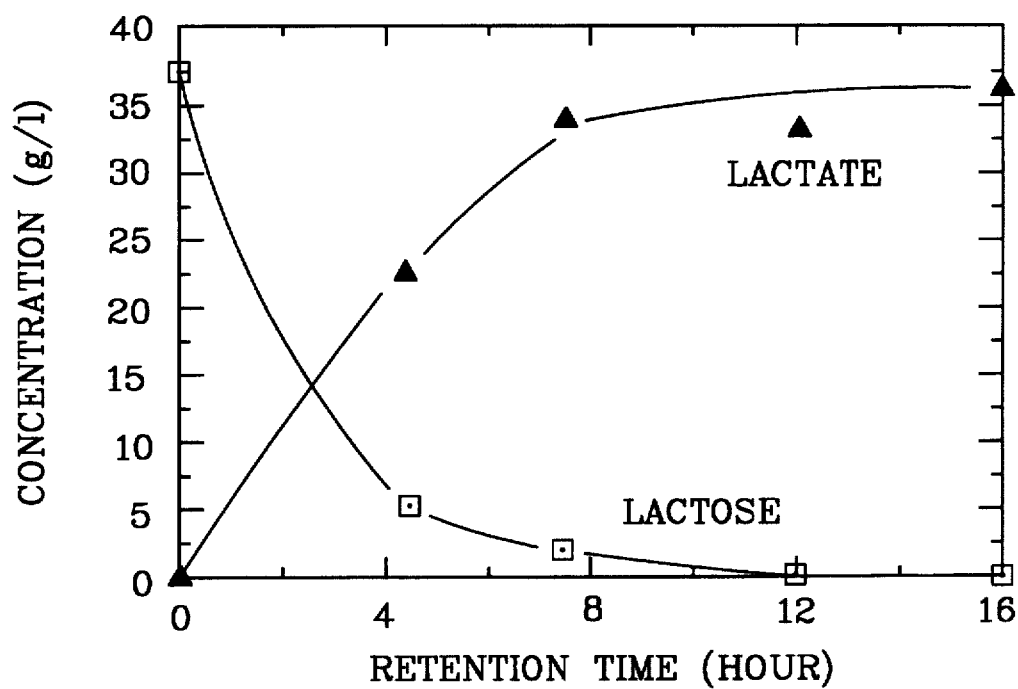

Typical continuous fermentation kinetics with *S. lactis* at pH 6.0 and 37° C. is shown in FIG. 4. The reactor was operated under well-mixed conditions at all retention times studied. FIG. 4a shows the results from a synthetic lactose medium. In FIG. 4b, sweet whey permeate was used as the feed substrate to the bioreactor. Complete conversion of lactose to lactic acid occurred at ~12 hours retention time. In contrast, batch fermentation with the same bacterium took more than three days to ferment whey lactose. The lactic acid yield from lactose was about 95% (wt/wt).

Figure 5:
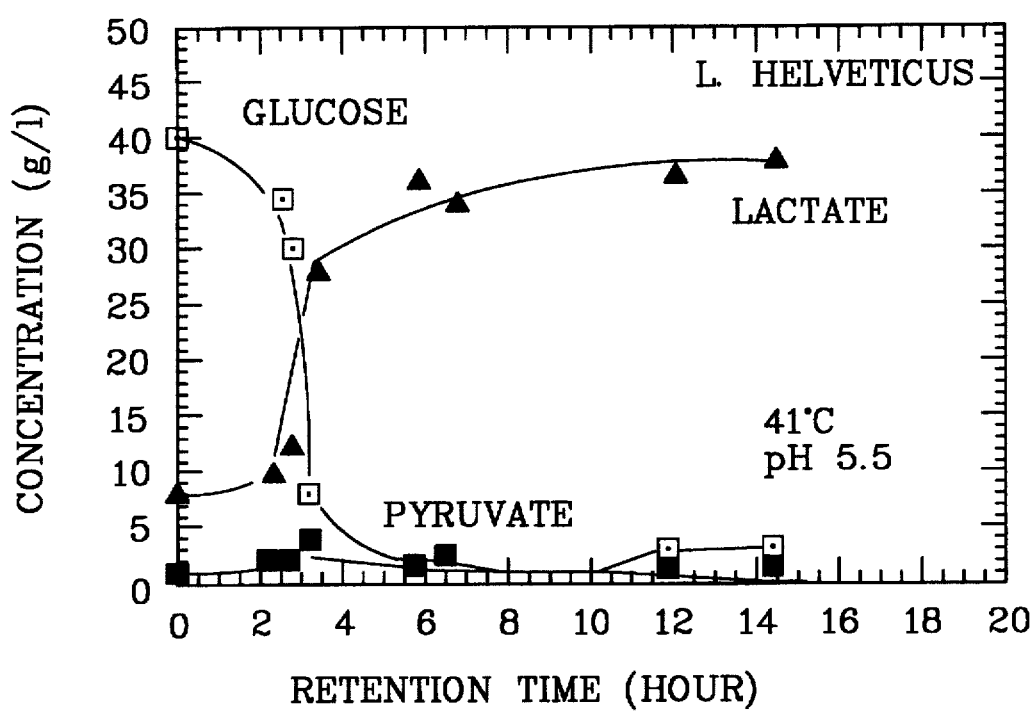
FIG. 5 is a graph showing the homolactic fermentation with *L. helveticus* for lactate production from acid whey using the method of the present invention.

Similar results were obtained from acid whey with *L. helveticus* at pH 5.5, 42° C. As shown in FIG. 5, complete lactose conversion to lactate occurred at ~6 hrs retention time with the continuous bioreactor. It took more than 4 days in batch fermentation. Also, there was significant accumulation of pyruvate in batch fermentation. The lactate yield from this bacterium was also ~95% (wt/wt). The lactic acid productivity from this bioreactor was higher than 6 g/hr-L reactor volume, which compares favorably with most prior studies with supplemented whey permeate. A higher productivity and higher lactate concentrations also can be attained with this bioreactor if a concentrated whey is used as the feed medium.

Both of these two bioreactors were able to maintain their productivity for a long period of continuous operation, more than 4 months. It is clear that the fibrous bioreactor is advantageous to use in lactic acid production from whey.

EXAMPLE 2

Homoacetic Fermentation of Lactate

Figure 6:
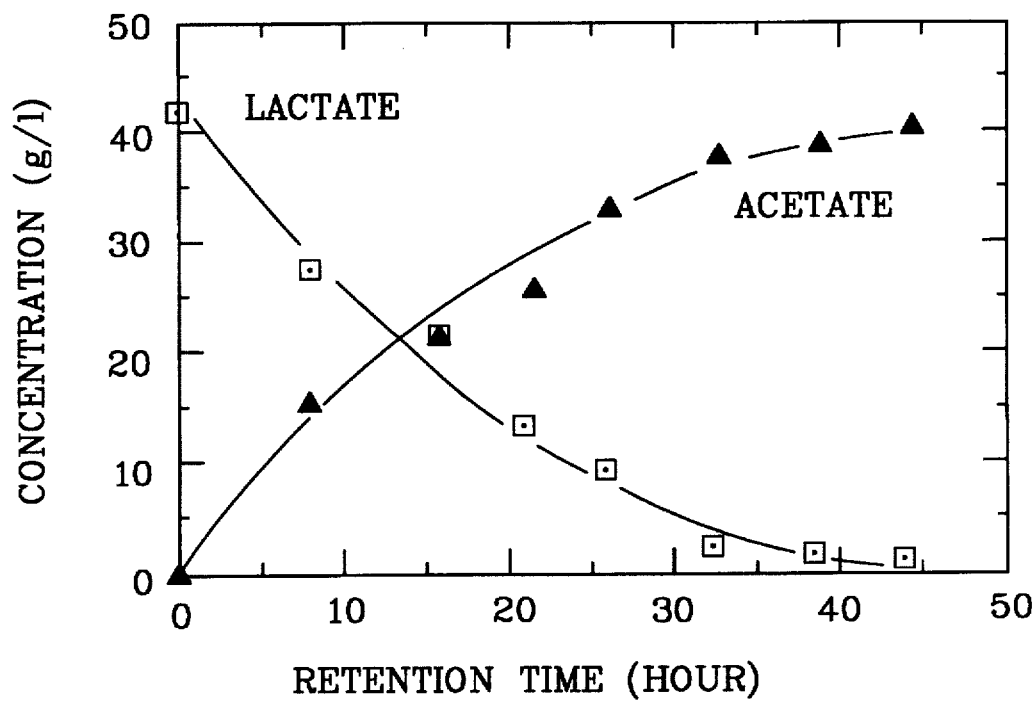
FIG. 6 is a graph showing the homoacetic fermentation with *C. formicoaceticum* for acetate production from lactate using the method of the present invention.

In the continuous bioreactor with *C. formicoaceticum* at pH 7.6, 37° C., using a synthetic lactate medium, it reached 4% acetate at less than 45 hrs retention time (FIG. 6). In batch fermentation with the same medium and culture, it took more than 5 days to reach the same acetate level. The acetate yield from lactate was ~96% (wt/wt). The results from the immobilized cell bioreactor are also superior to most prior homoacetic fermentation studies with *C. thermoaceticum* grown in synthetic glucose media, which normally takes several days to reach 2% acetate with only 80% yield from glucose.

EXAMPLE 3

Co-cultured Fermentations for Acetate Production from Lactose

Figure 7:
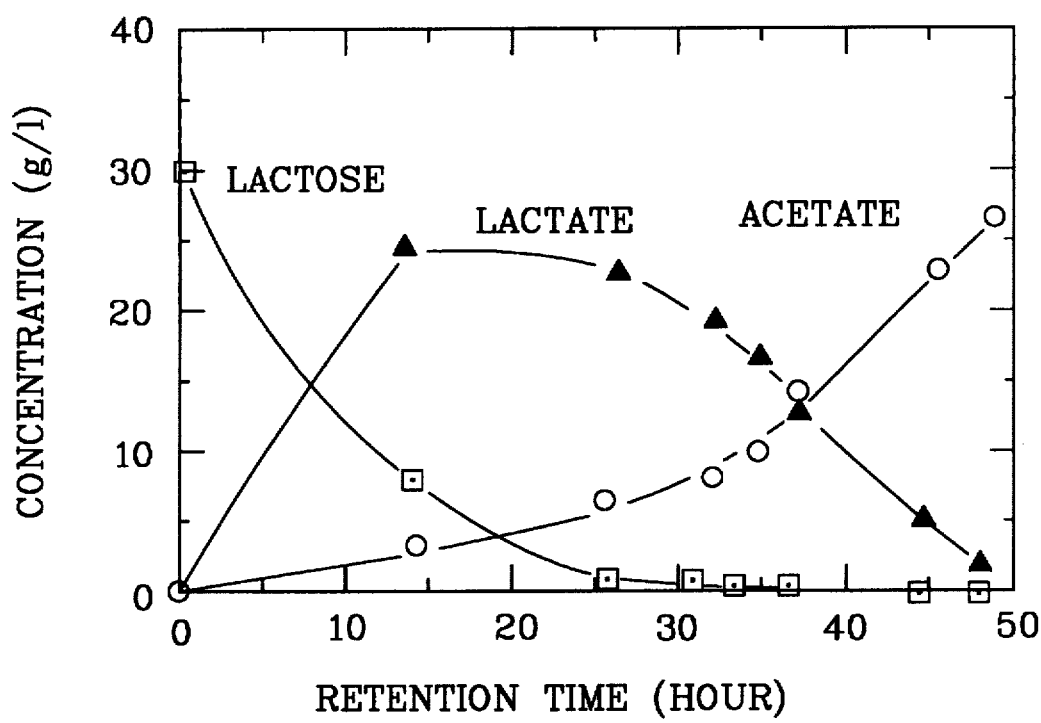
FIG. 7 is a graph showing a co-cultured fermentation for acetate production from lactose with *S. lactis* and *C. formicoaceticum* co-immobilized in the bioreactor of the present invention.
Figure 8:
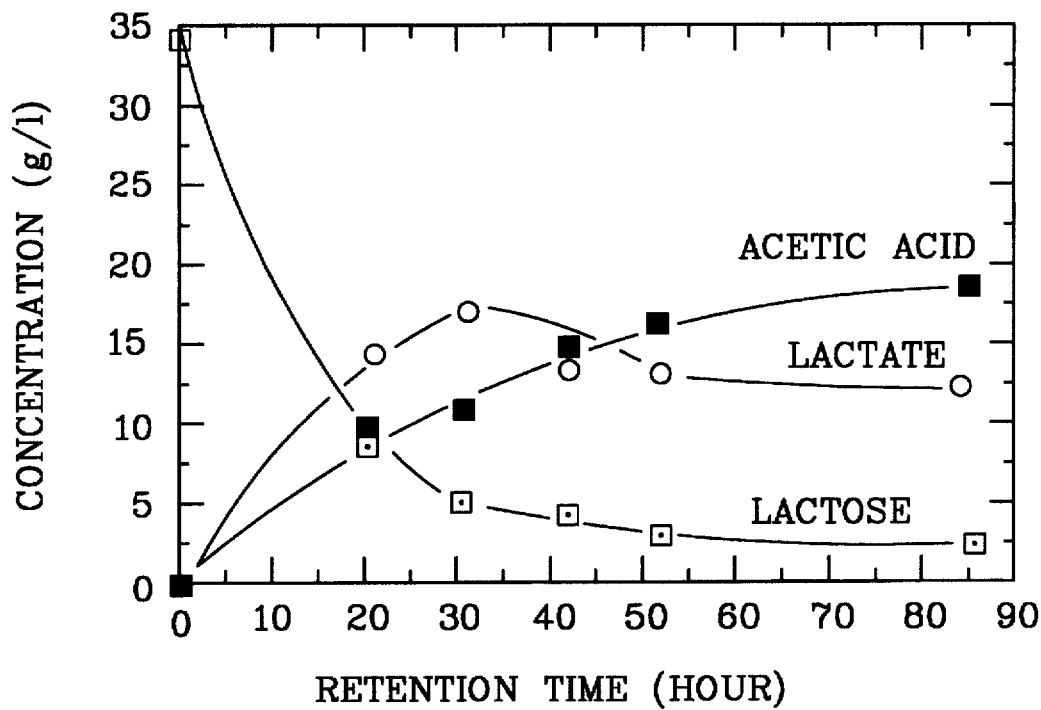
FIG. 8 is a graph showing a co-cultured fermentation for acetate production from lactose in plain whey permeate with S. lactis and C. formicoaceticum co-immobilized in the bioreactor of the present invention.

To produce acetate from lactose, both *S. lactis* and *C. formicoaceticum* were co-immobilized in the same bioreactor. FIGS. 7 and 8 show the fermentation kinetics with a lactose synthetic medium and with whey permeate, respectively. Both were operated at 37° C., pH 7.6. Plain whey permeate did not have sufficient nutrients to allow the fermentation to complete. However, both fermentation rate and conversion improved significantly when yeast extract and trypticase were added to supplement whey permeate. Other nutrient sources, such as corn steep liquor, also may be used to achieve the same effect.

EXAMPLE 4 propionic acid fermentation

Propionic acid fermentation with lactate as the substrate was studied first. The immobilized cell bioreactor was operated at 30° C. However, no external pH control was needed when lactate was used as the substrate for fermentation. This is because about equimolar acid products are formed with lactate, and the pH change in the bioreactor due to fermentation of lactate to propionate was small (only about plus or minus 0.3 pH unit). It took about 20 days for the new bioreactor packing to be saturated with cells and to reach steady state.

The synthetic medium used to grow the bacterium contained (per liter); 10 g yeast extract (Difco), 5 g trypticase (BBL), 0.25 g $K_2HPO_4$, 0.05 g $MnSO_4$, and 40 g lactate (0.44M sodium lactate). The media used to feed the bioreactor were prepared from tap water and contained 40 g/L lactate and various amounts of yeast extract (1–10 g/L) and trypticase (0–5 g/L). The medium pH was adjusted to a desired value by adding 6N HCl or NaOH. All media were heat sterilized at 121° C. and 15 psig for 20 min before use.

The spiral wound fibrous bed bioreactor was successfully used to perform continuous propionic acid fermentation. A high cell density of 37 g/L was attained in the reactor and that contributed to a high reactor productivity of about 4 times higher than that from a conventional batch propionic acid fermentation. Also, the immobilized cell bioreactor can accept low-nutrient and low-pH feed without sacrificing much in reactor productivity. This bioreactor was operated continuously for several months without encountering any operational problems such as clogging, degeneration, or contamination.

Further details to the above experiment are available from the article "Continuous Propionic Acid Fermentation by Immobilized *Propionibacterium acidipropionici* in a Novel Packed-Bed Bioreactor" by Vivian P. Lewis and Shang-Tian Yang in Biotechnology and Bioengineering Vol. 40, 1992. Such publication is incorporated herein.

Figure 9:
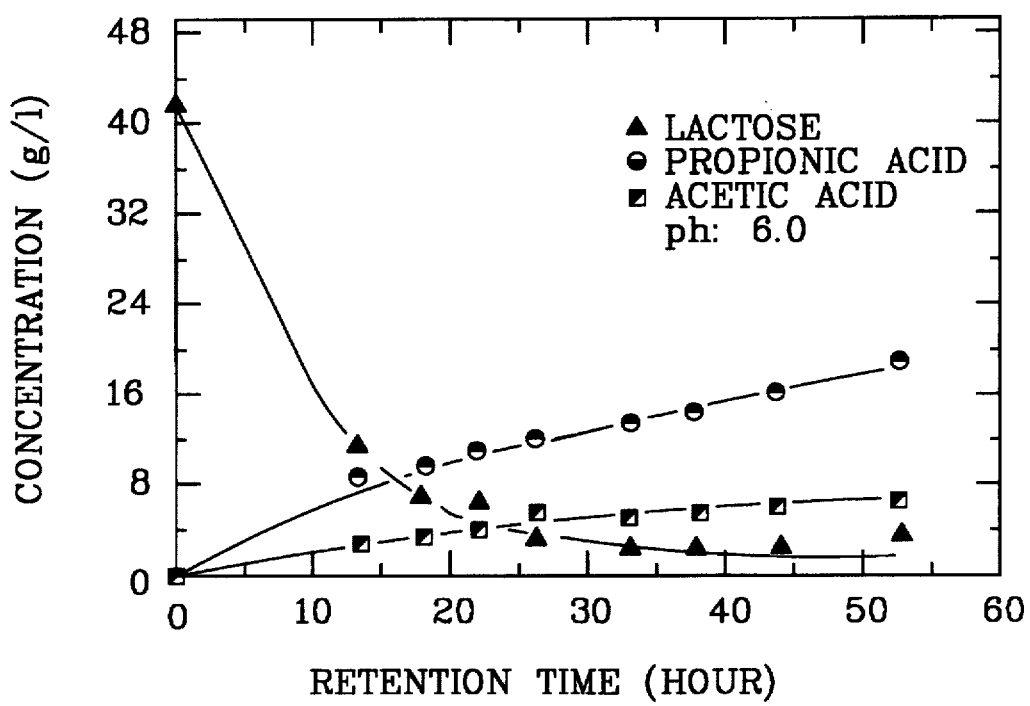
FIG. 9 is a graph showing the concentration profiles of lactose, propionic acid, and acetic acid versus the reactor retention time for propionic acid fermentation of plain whey permeate with P. acidipropionici at pH 6.0 and 30° C.

Further experiments were then conducted with sweet whey permeate as the feed to the bioreactor. The reactor pH was controlled at a constant level around 6.0. FIG. 9 shows typical concentration profiles of lactose, propionic acid and acetic acid versus the reactor retention time for fermentation at pH 6.0 and 30° C. It was found that significant amounts of succinic and pyruvic acids were also produced from lactose during propionic acid fermentation. As also can be seen in FIG. 9, lactose fermentation was fast at low retention time (<20 hrs) where propionic acid concentration was low (<1%). At higher retention times, the fermentation slowed down due to propionic acid inhibition. However, more propionic acid could be produced from lactose fermented when cell growth was slower.

The product yields, based on the initial lactose concentration present in the whey permeate, reached 46% for propionic and 15% for acetic acid at 52 hrs retention time. The propionic acid yield was about 85% of the theoretical yield (54.8%) from glucose. This result is also much better than that can be obtained from batch fermentation, which usually takes more than one week to complete.

Similar results were obtained with de-lactosed whey permeate (containing ~10% lactose) and whey permeate mixture at ~1:2 ratio. Also, no significant difference was found with NaOH or CaO used as the base in controlling the reactor pH.

Whey permeate may not have sufficient nutrients to support cell metabolism and growth. The required retention time to reach a high conversion can be significantly shortened if whey permeate is supplemented with, for example, yeast extract to provide additional nutrients for cell growth.

Figure 10:
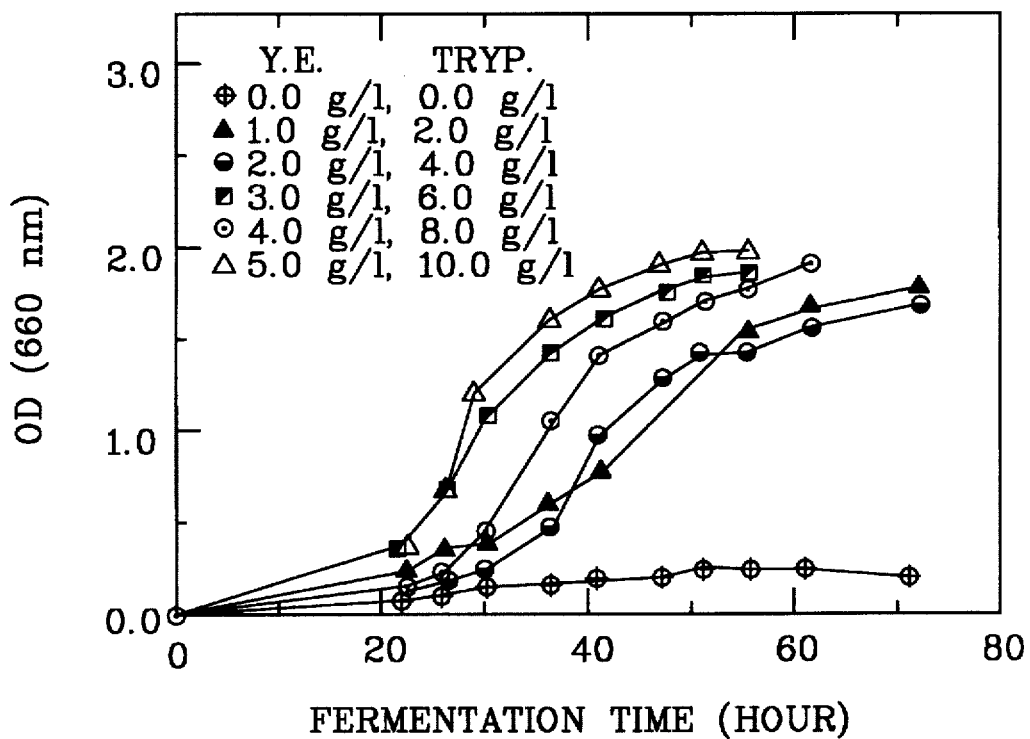
FIG. 10 is a graph showing that when whey permeate is used without nutrients supplement no cell growth is observed for propionibacterium for a period of 70 hours.

When a synthetic medium was used, relatively high concentrations of yeast extract and trypticase were found to be essential to batch fermentation. Whey permeate supplemented with various amounts of yeast extract and trypticase was studied. As shown in FIG. 10, in batch culture without nutrients supplement, no cell growth was observed for propionibacterium for a period of 70 hours. Furthermore, cells generally grew faster with higher concentrations of yeast extract and trypticase, which enhance cell growth and fermentation rate.

For continuous fermentation with immobilized cells, yeast extract (YE) and trypticase (Tryp) were added to whey permeate to see if they would have any effects on propionic acid production. In this study, the reactor was operated at 35 hrs retention time, pH 6.5, and 30° C., but the feed was changed from plain whey permeate to that with different nutrient supplementation levels. The outlet product concentrations at steady state from feed with three different nutrient levels are compared in Table 1. Apparently, both the fermentation rate and product yields increased slightly with increasing the nutrient level. At the highest nutrient level studied, propionic acid concentration reached 27 g/L, which was equivalent to 54% yield. This indicates that the fermentation economics can be improved significantly if a cheap nutrient supplement can be used.

TABLE 1

Effect of Supplemental Nutrients on Propionic Acid Fermentation.

| Nutrient Level (g/L) | | | Outlet Concentration (g/L) | | |
| --- | --- | --- | --- | --- | --- |
| YE | Tryp | O.D. | Propionate | Acetate | Succinate |
| 0 | 0 | 8.9 | 23.1 | 8.8 | 7.5 |
| 5 | 10 | 10.8 | 24.1 | 9.7 | 6.8 |
| 10 | 20 | 12.8 | 27.4 | 10.0 | 5.5 |

The difference in fermentation rate between the lowest (no supplementation) and the highest nutrient level was not very significant. Apparently, the supplemental nutrients are not essential to propionic acid production from whey permeate. For continuous, immobilized cell bioreactors, reactor productivity is dependent on active cell density only, not cell growth. Therefore, a minimal level of growth nutrients should be used in the feed to lower the raw material costs and to minimize cell production, but still maintain cell activity. This also allows more substrate (carbon source) to be converted to their metabolic products (propionic and acetic acids) since less carbon source will be incorporated into cell biomass.

Figure 11:
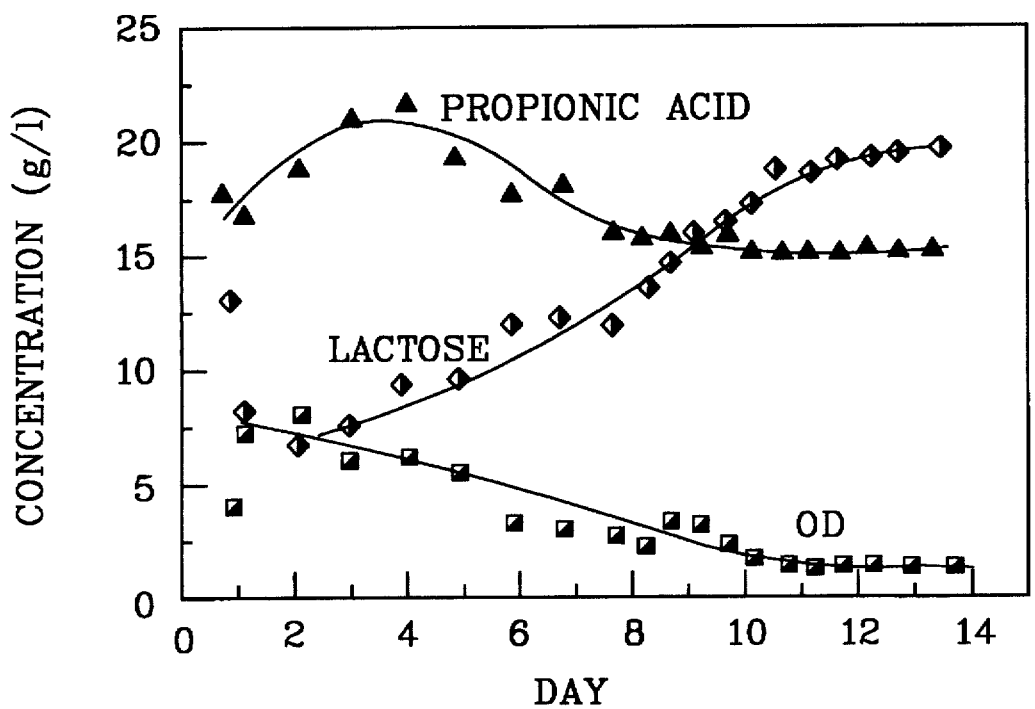
FIG. 11 is a graph showing the long-term reactor stability in propionic acid production from whey permeate using the method of present invention.

Long-term reactor stability during continuous fermentation with plain whey permeate as the feed substrate was also studied. The bioreactor was initially started up and fed with a rich, synthetic medium containing 2% lactose. The reactor was operated under well-mixed conditions, at pH 6.5, 30° C., and at a fixed retention time of ~29 hrs. Then, the reactor feed was switched to whey permeate. The effluent samples were taken twice per day for two weeks. As shown in FIG. 11 after feed switch, propionic acid production increased initially, but then decreased gradually until a new steady-state value was settled. The cell density, as measured in OD (optical density), followed a similar trend, while the lactose concentration had an opposite response to the feed switch. This dynamics indicated that cell growth activity was reduced to a much lower level (~20% of the high) when plain whey permeate was used for long term operation. The low growth activity was also reflected in the low (zero) pyruvate concentration. The reduced cell growth activity apparently had also reduced the fermentation rate, as indicated by the lower propionic acid production. However, the reduction in propionic acid production rate was only 25%, and after reaching the new steady state, the reactor seemed to be able to maintain its productivity with plain whey permeate. This indicates that plain whey permeate, without nutrient supplementation, would be acceptable as the feed substrate for long-term, continuous propionic acid production using the immobilized cell bioreactor.

In this study the propionic acid yield, based on lactose consumption, was ~52%, which was slightly higher than the values (~46%) obtained from the kinetic study. This indicates that reduced cell growth may provide some advantage in substrate utilization.

The concentration of immobilized cells in the fibrous bed bioreactor was observed to be very high, ranging from 30 g/L to 60 g/L for the fermentations studied. The variation came from different cultures and different growth conditions. The high reactor productivity from these bioreactors can be attributed to the high cell density in the reactor. It was observed that cells were immobilized in the fibrous material by both attachment through surface colonization and entrapment of large cell clumps within the fibrous matrix. This immobilization scheme allows cells to be swept from the matrix and thus achieves constant renewal of cell population within the bioreactor. This ensures the reactor to maintain a stable, long-term productivity, and not to degenerate due to cell aging.

It is concluded that plain whey permeate does not contain sufficient nutrients to support fast cell growth for most of the bacterial cultures studied in above examples. Nutrient supplementation is particularly important for batch and continuous processes requiring fast cell growth. Thus, without nutrient supplementation, whey may not be a good substrate for use in conventional fermentation processes. Consequently, almost all previous whey fermentation studies supplemented whey or whey permeate with yeast extract, corn steep liquor, soy meal or molasses in order to get reasonably good results. However, with the fibrous bed bioreactor, the immobilized cells were able to ferment whey lactose efficiently, even in plain whey permeate. This is due to the high cell density maintained and the reduced cell growth activity required in the immobilized cell bioreactor. Thus, no nutrient supplement is required, except maybe for reactor start-up.

It is noted that all the fermentations presented in these examples are subject to significant product inhibition. In the bioreactor experiments, the reactor was operated under well-mixed conditions and was thus subjected to the worst inhibition conditions. If the reactor was operated under optimal plug-flow conditions, the required retention time for complete. fermentation would be significantly shorter. Thus, the bioreactor can be operated at other modes to further improve the process efficiency.

It is also noted that the bioreactor needs not be operated as a continuous bioreactor. It also can be operated as a batch or fed-batch bioreactor, or used as a breeder for batch fermentation. Batch fermentation is the industry standard for most fermentations and has its advantages over continuous process in some aspects. The following example demonstrate its application in this fashion.

EXAMPLE 5

Sequential Batch Fermentation

The immobilized cell bioreactor was connected to a 5-liter agitated fermentor and the whole system was operated at sequential batch fashion. In this experiment, the flask 330 of FIG. 3 was replaced with the 5-liter fermentor and the feed line to the bioreactor was closed. The fermentor was autoclaved, and then filter-sterilized whey permeate was pumped into the fermentor. Three liters of the whey permeate was used in each batch fermentation and the fermentation was run just like conventional batch experiment except that the fermentor content was circulated through the immobilized cell bioreactor. After several days fermentation when complete conversion is achieved, the fermentor content was replaced with new whey permeate and a new batch was thus started at that point.

Figure 12:
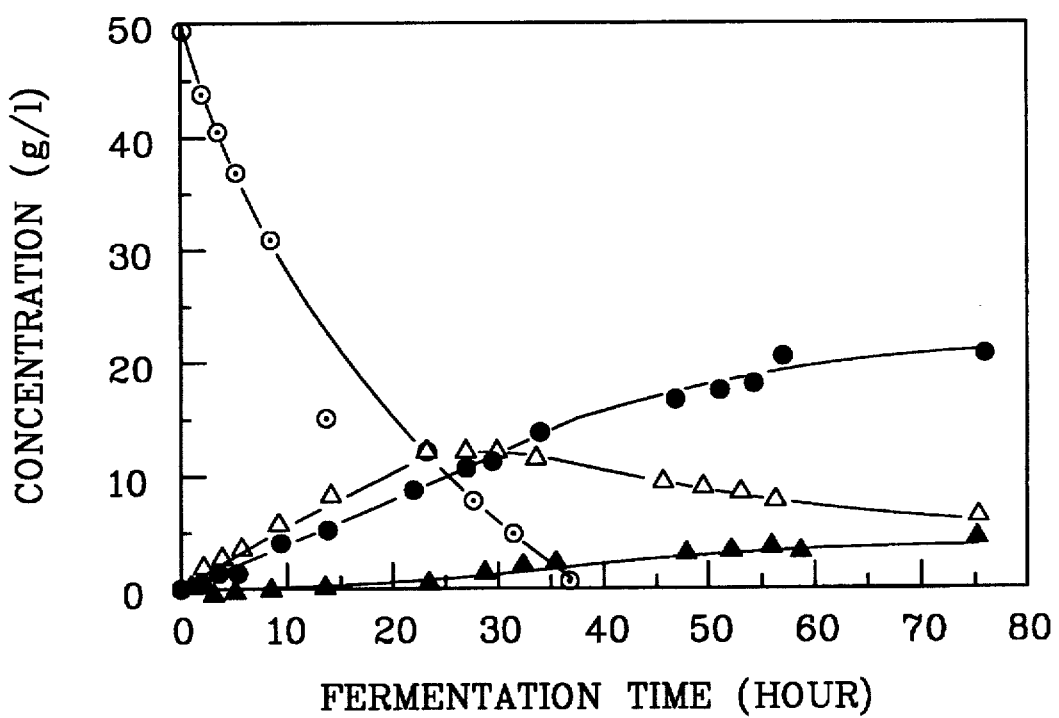
FIG. 12 is a graph showing the kinetics of a batch propionic acid fermentation of whey lactose with S. lactis and P. acidipropionici co-immobilized in the bioreactor at pH 6.0 and 37° C.

FIG. 12 shows a typical batch result from fermentation with de-lactose whey permeate and whey permeate mixture at pH 6.5, 37° C. The immobilized cell bioreactor used in this study contained co-cultures of *S. tactis* and *P. acidipropionici*, and has a liquid volume of ~450 mL. It took about 60 hrs to attain 2% propionic acid. Also, higher propionic acid concentrations can be attained with higher initial lactose concentrations. Up to 5% propionic acid concentration was reached. A higher product concentration would render its recovery and concentration easier and less costly. These results show that conventional batch fermentation process can be significantly improved by using the immobilized cell bioreactor as a breeder.

Therefore, propionic acid, acetic acid, and lactic acid all can be produced efficiently from whey permeate or similar streams by using the immobilized cell bioreactor of the present invention. The results obtained from these bioreactors are far superior to the conventional batch fermentor employing free cells.

EXAMPLE 6

Organic Acid Extraction

Figure 13A:
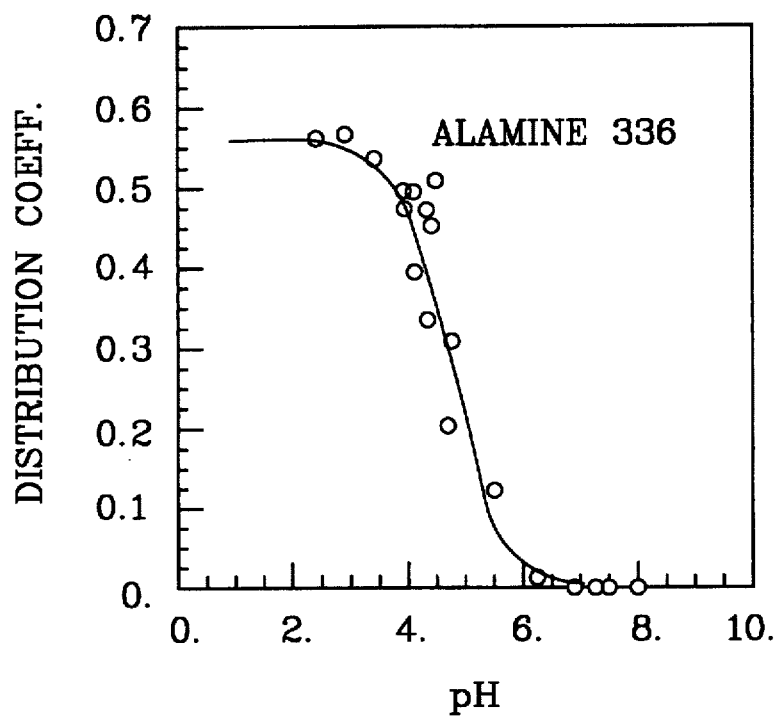
FIGS. 13a and 13b are graphs showing the effect of pH on the distribution coefficient for acetic acid extraction using Alamine 336 and Aliquat 336.
Figure 13B:
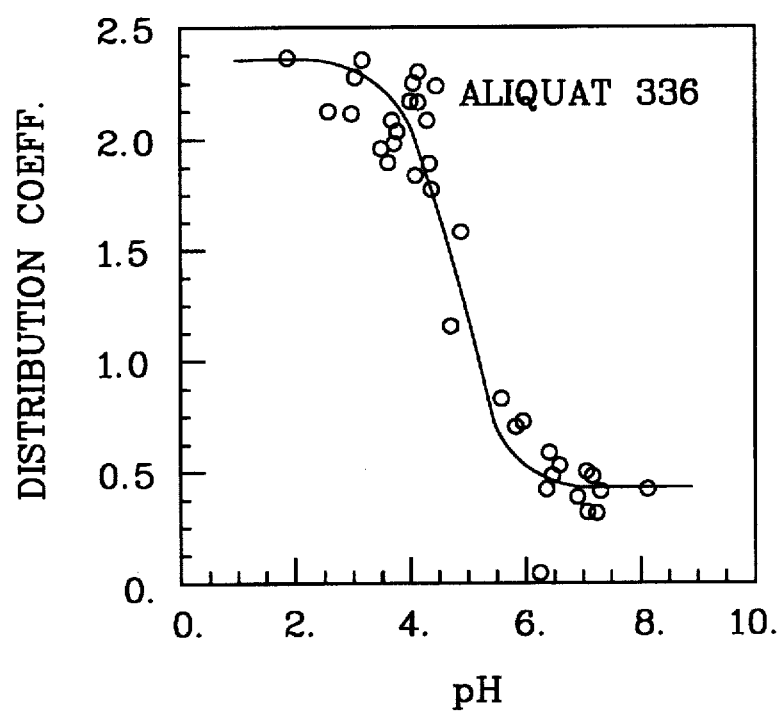

Two aliphatic amine extractants, one tertiary amine and one quaternary amine, were employed to extract organic acids, including acetic, propionic, lactic, and butyric acids, from their aqueous solutions, including fermentation broth, and to study their abilities to extract organic acids at various pH values. These extractants, Alamine 336 and Aliquat 336, are products of the Henkle Corporation. Two diluents, 2-octanol (polar) and kerosene (nonpolar) were investigated for their abilities to increase the extracting power of the amine extractants. The extraction coefficient, Kd, was found to be greatly affected by the solution pH, as shown in FIG. 13. In general, the Kd value increases with a decrease in the pH value except at extremely high or low pH where Kd does not change with the pH. Aliquat 336 (quaternary amine) extracts both undissociated and dissociated acids, and thus can be used under both acidic and basic conditions. Alamine 336 extracts only the undissociated acid and does not extract the acid under basic conditions. In general, the Kd values are higher for longer chain carboxylic acids. In other words, the extractant prefers butyric acid to propionic acid, and to acetic acid. Lactic acid has about the same Kd values as acetic acid. Details about these experiments are fully described in an article entitled "Extraction of Carboxylic Acids with Tertiary and Quaternary Amines: Effect of pH" by Shang-Tian Yang et. at appearing in the publication Industrial & Engineering Chemistry Research, vol. 30, pages 1335–1342, 1991.

Figure 14A:
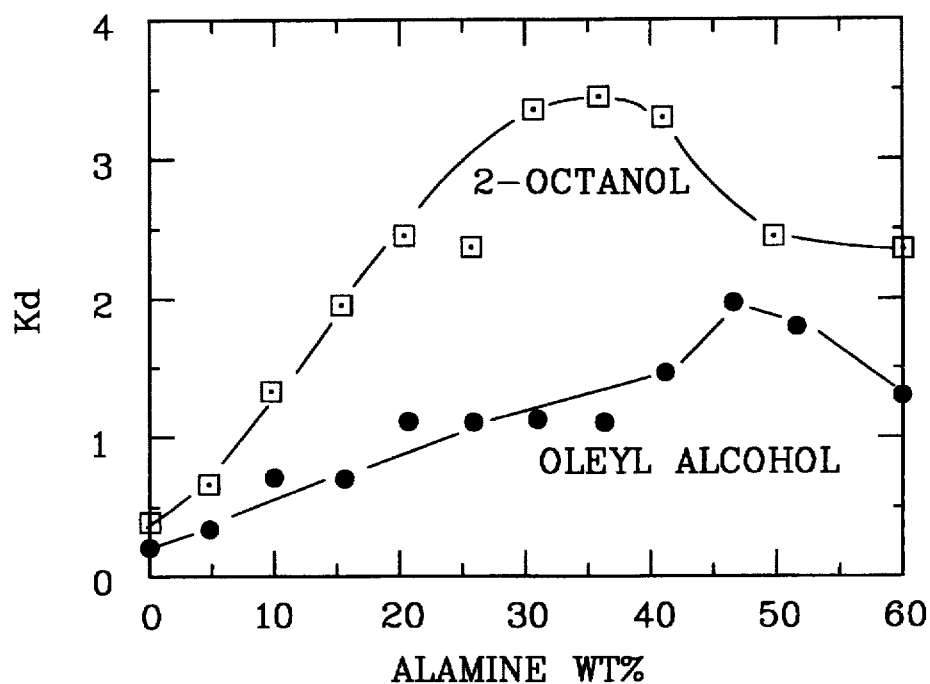
FIGS. 14a and 14b are graphs showing the effect of diluent on the distribution coefficient for acetic acid and lactic acid, respectively, using Alamine 336.
Figure 14B:
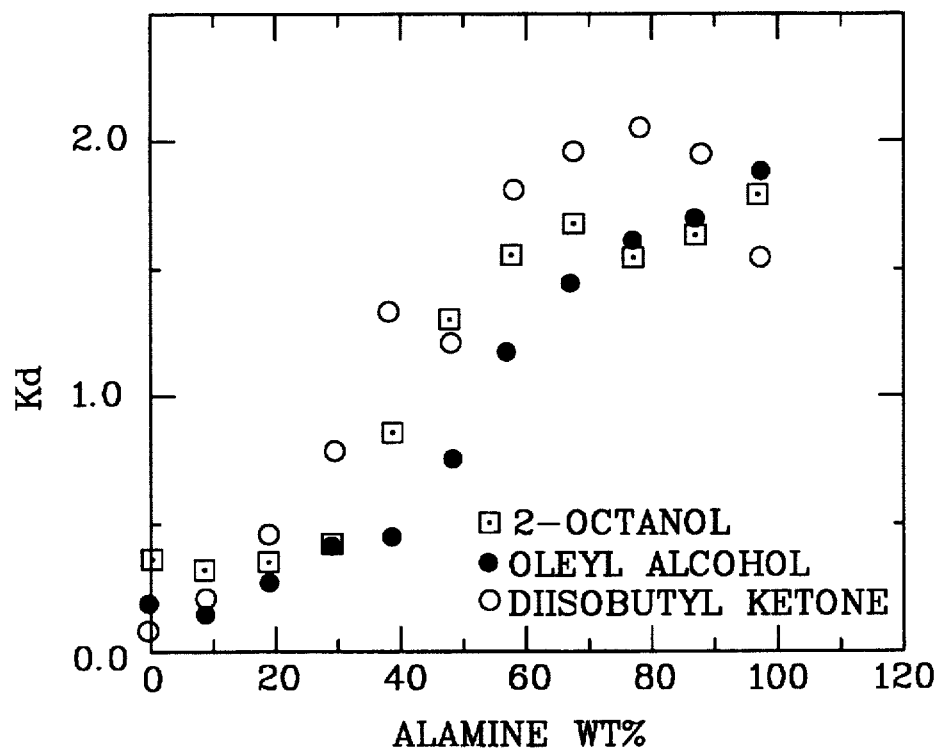

The use of a polar diluent was found to be beneficial to extraction with Alamine 336. Further experiments were conducted to study the effect of several polar diluents on the extractant Alamine 336. Oleyl alcohol and 2-octanol were studied for acetic acid extraction. FIG. 14a shows that 2-octanol is better than oleyl alcohol, and ~35% Alamine 336 in 2-octanol gave the highest Kd value. A third diluent, diisobutyl ketone was also used in studying lactic acid extraction. FIG. 14b shows that diisobutyl ketone was the best one among the three studied, and 80% of Alamine 336 gave the highest Kd value.

Figure 15:
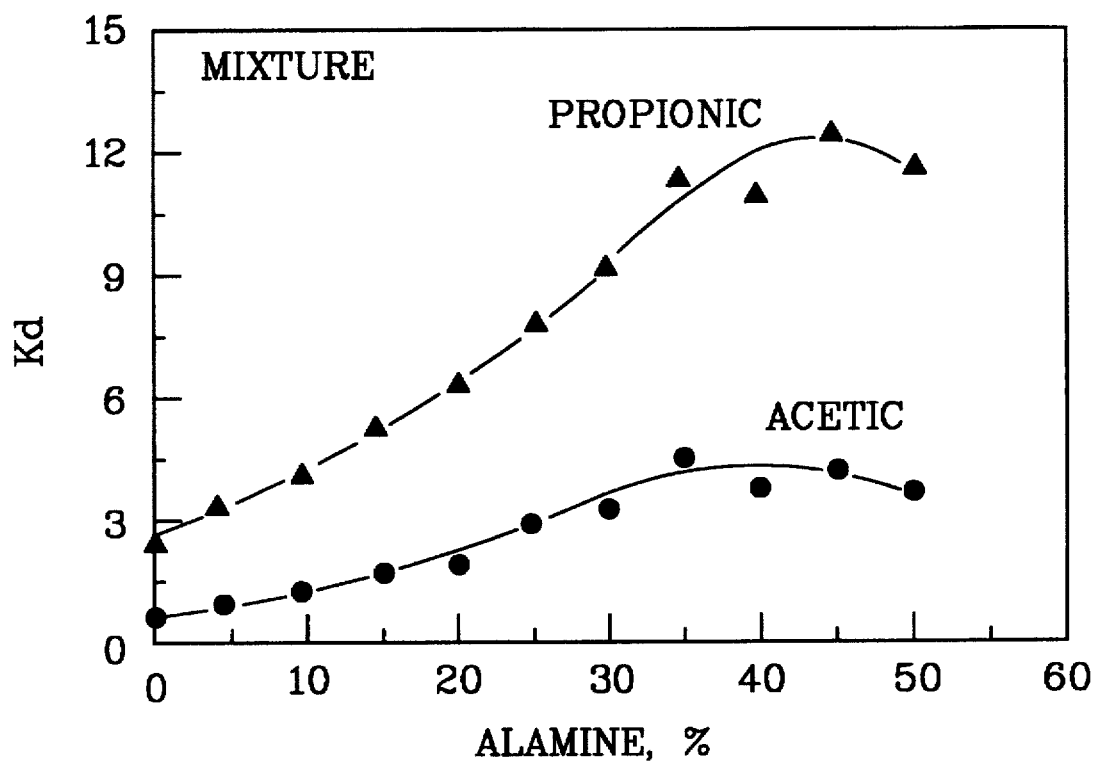
FIG. 15 is a graph showing the distribution coefficients for propionic acid and acetic acid extraction with Alamine 336 in 2-octanol.

Another experiment was conducted to study the extraction of propionic acid and acetic acid mixture with Alamine 336. As shown in FIG. 15, the Kd value for propionic acid is always greater than the Kd value for acetic acid. This indicates that the mixed organic acids can be separated and purified with extraction using Alamine 336.

Further experiments were conducted to study extraction of lactic acid from the fermentation broth obtained from acid whey fermentation with *L. helveticus* described in Example 1. A packed bed column extractor was used. The extractant, 80% Alamine 336 in diisobutyl ketone, and the broth containing lactic acid were fed counter-currently through the extractor. The extractant containing lactic acid was collected at its outer from the extractor and was then fed to another extractor where a NaOH solution was used to back-extract lactic acid from the extractant. HPLC was used to analyze the acid content in aqueous streams. Results showed that up to 40% lactic acid present in the fermentation broth was extracted to the extractant and 100% of the acid in extractant was back-extracted into the NaOH solution with one-pass contact. Thus, dilute lactic acid can be efficiently recovered as concentrated sodium lactate using the described two-step extraction method.

Similar extraction experiments were conducted with acetic acid extraction with 40% Alamine 336 in 2-octanol. At a feeding rate equivalent to 2-hr retention time in the column extractor, ~80% of the acetic acid present in the aqueous phase was extracted into the extractant. Back-extraction with CaO suspension was then conducted in a beaker with mixing. Results showed that all acetic acid in the extractant was recovered as calcium acetate. Similar experiments were conducted with CaO/MgO mixture in suspension, and the resulting extraction product was CMA or calcium acetate/ magnesium acetate mixture. The extractant regenerated from back-extraction showed the same extraction performance as that of fresh extractant. Thus, the two-step extraction method described in this invention can be used to efficiently recover acetic acid from a dilute fermentation broth as a concentrated acetate salt solution.

EXAMPLE 7

Extractive Fermentation for Ethanol Production from Whey

Figure 16A:
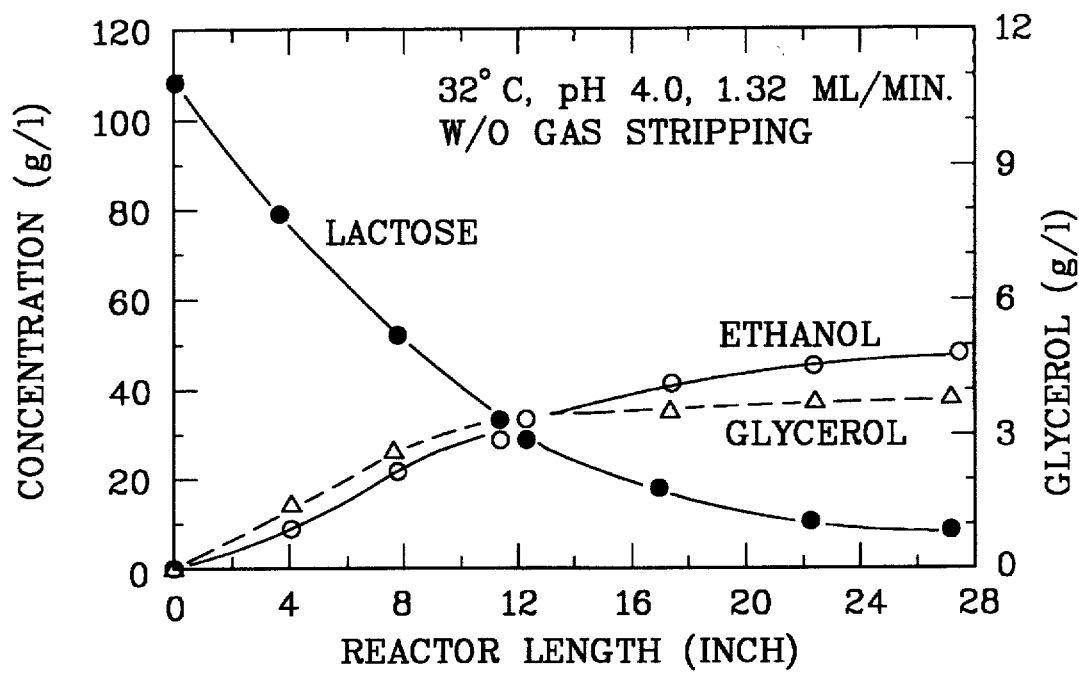
FIGS. 16a and 16b are graphs showing ethanol production from concentrated whey permeate in the fibrous bed bioreactors with and without $CO_2$ stripping, respectively.
Figure 16B:
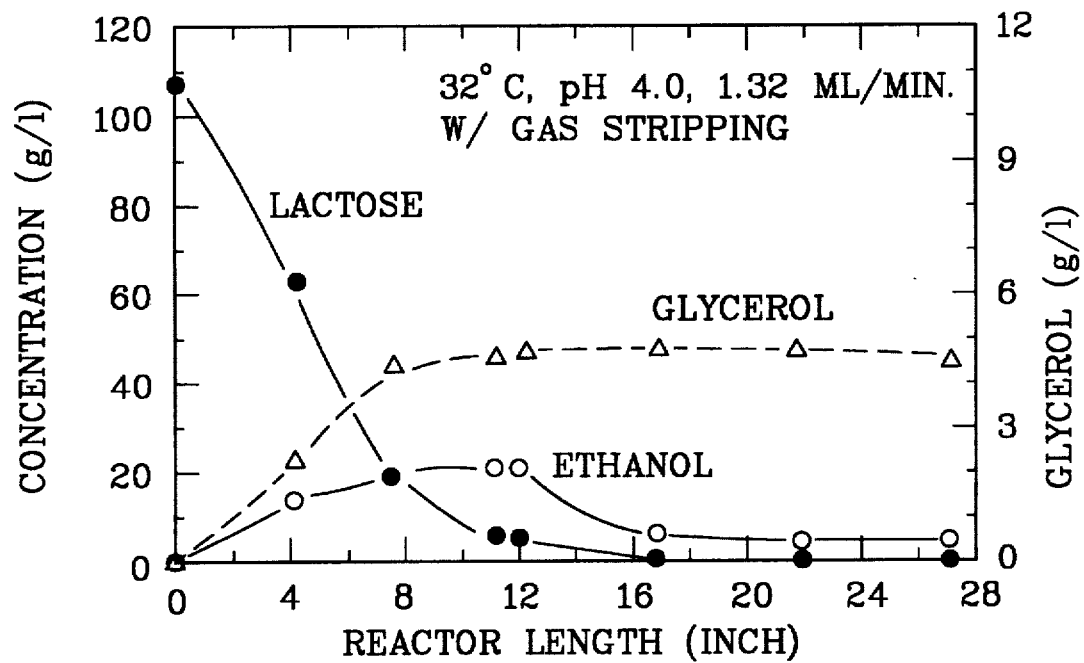

In this example, the use of the convoluted fibrous bioreactor of the present invention to ethanol production from whey permeate was described. Concentrated whey permeate containing about 10% lactose was used to feed the bioreactor. The bioreactor was constructed in a similar fashion as described earlier, but here the cotton towel was topped with a layer of 0.25 in. ceramic saddles and then spirally wound and packed in a column. The ceramic saddles were used as spacers to keep adjacent spiral layer apart. No liquid recirculation was used in this case. The bioreactor was inoculated with the yeast *Kluvoromyces fragilis* and then fed with the whey permeate, which has a pH value of ~4.0. The temperature was maintained at 32° C. Samples from various positions along the reactor length was taken and analyzed with HPLC. A second bioreactor was constructed in similar way, but was operated as a trickle bed with continuous $CO_2$ circulation through the bioreactor to strip ethanol from the reactor. The results from these two bioreactors at steady state are shown in FIG. 16. As shown in FIG. 16a, without gas stripping, 5% ethanol was obtained and there were still some lactose left in the effluent. The ethanol productivity was ~8 g/hr-L reactor volume. With gas stripping shown in FIG.

16b, the ethanol concentration in the liquid medium was kept low due to stripping into the gas phase, resulting in a much faster fermentation rate. Consequently, all lactose present in the feed whey permeate was fermented by the time it reached ~60% of the reactor length. The ethanol productivity was ~18 g/hr-L reactor volume. The cell density found in these bioreactors was ~80 g/L. These experiments indicates that the fibrous bed bioreactor was advantageous for ethanol fermentation, especially with gas stripping.

EXAMPLE 8

Continuous Production of GM-CSF

Figure 17:
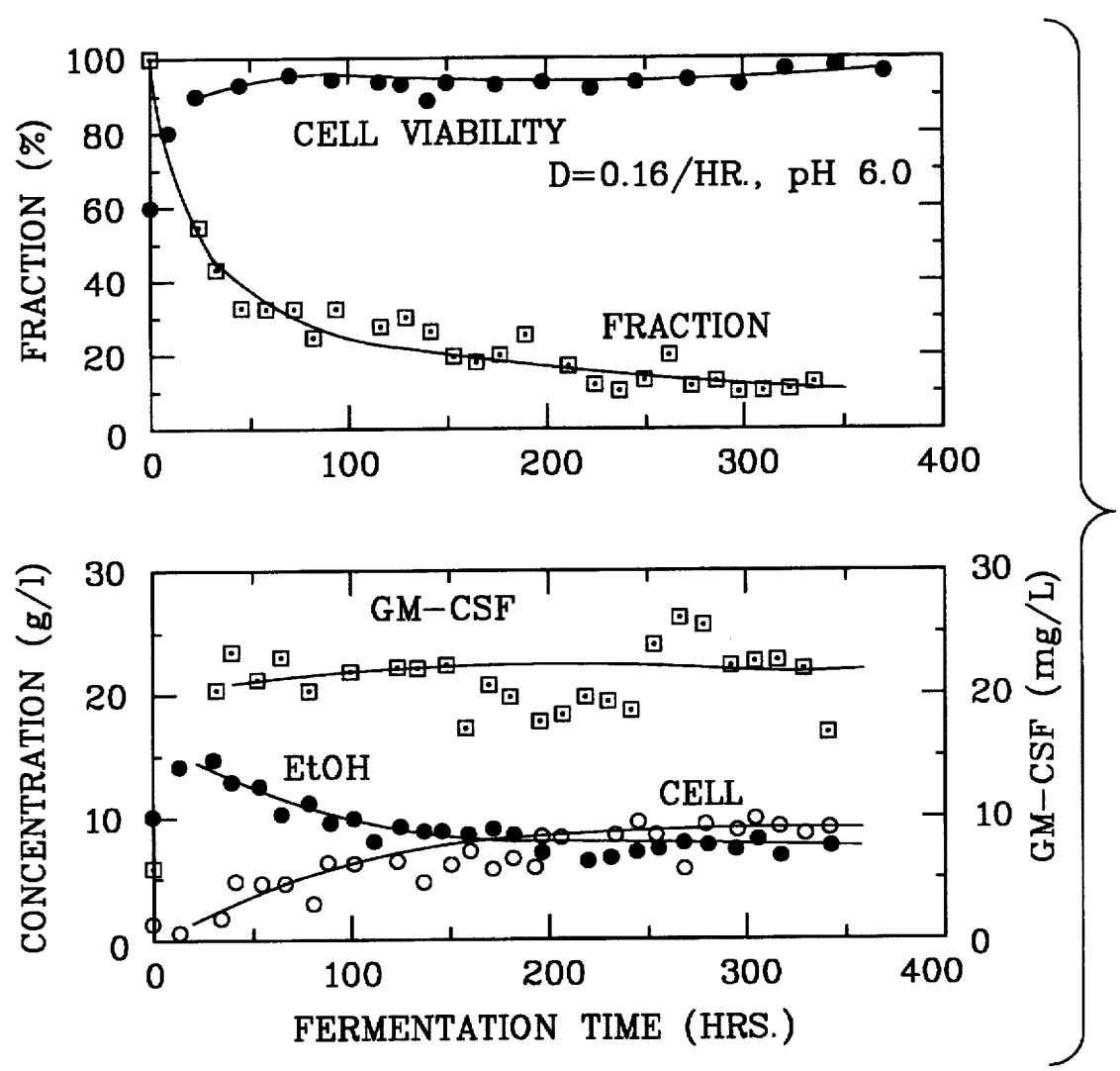
FIG. 17 is a graph showing kinetics of a continuous recombinant yeast fermentation for GM-CSF production using the fibrous bed bioreactor of present invention.

An aerobic fermentation with recombinant yeast *Saccharomyces cereviciae* to produce a recombinant protein, murine granular macrophage-colony stimulating factor (GM-CSF) was conducted using the fibrous bed bioreactor. Air was sparged through the gap between spiral fibrous layers in the reactor, constructed following the description given in the present invention. A synthetic medium containing ethanol as the carbon source was used as the feed medium to the bioreactor. The results are shown in FIG. 17. It was found that even with a non-selective medium, stable, continuous production of GM-CSF over 400 hrs or longer can be achieved with this bioreactor. This long stable production of a recombinant protein product is difficult, if possible, to achieve with conventional continuous bioreactors due to plasmid instability problem. More details about the experiment can be found in a Ph.D. dissertation titled "Multiphase Bioreactors for Recombinant Yeast Fermentation" by Chin-Hang Shu of Ohio State University published in December, 1992. This example shows the application of the bioreactor of the present invention in aerobic fermentation for biochemicals (protein) production.

It is clear that the present invention will have broad applications in the production of biochemicals, including organic acids, organic salts, alcohols, proteins, and other biochemicals with appropriate cultures, including bacteria, yeasts, molds, plant cells, and animal cells. Having thus described the invention in its preferred embodiment, it will be clear that modifications may be made without departing from the spirit of the invention. Also the language used to describe the inventive concept and the drawings accompanying the application to illustrate the same are not intended to be limiting on the invention rather it is intended that the invention be limited only by the scope of the appended claims.

I claim:

1. A packed bed support structure for bringing an organic reactant containing fluid into intimate contact with reactive cells comprising, in combination:

a) a housing provided with at least one inlet and at least one outlet:

b) a sheet material comprising cotton cloth having a porous fibrous matrix forming interior void spaces capable of entrapping at least a portion of said reactive cells, said sheet material being disposed within said housing in a sufficiently loosely convoluted configuration to provide gaps between outer surfaces of said convoluted sheet material of sufficient size to allow said reactant containing fluid to flow through said said gaps from said at least one inlet to said at least one outlet in intimate communication with said outer surfaces of said sheet material and said interior void spaces within said fibrous matrix.

2. The structure of claim 1 wherein said sheet material is convoluted into the shape of a wound spiral.

3. The structure of claim 2 wherein a hollow core open at both ends extends through the center of said spiral so that a fluid can be caused to flow through said hollow core.

4. The structure of claim 3 wherein said sheet material consists essentially of cotton cloth.

5. The structure of claim 3 wherein said material is terry cloth.

6. The structure of claim 3 wherein said material is gauze.

7. The structure of claim 2 wherein said sheet material consists essentially of cotton cloth.

8. The structure of claim 1 wherein said sheet material is convoluted into the shape of folded sheet material.

9. The structure of claim 1 wherein said sheet material is convoluted into the shape of laminated sheet material.

10. The structure of claim 1 wherein said sheet material is convoluted into the shape of corrugated sheet material.

11. The structure of claim 1 wherein a hollow core open at both ends extends through the sheet material substantially parallel to said gaps and positioned in respect to at least one said inlet and at least one said outlet so that a fluid can be caused to flow through said hollow core.

12. The structure of claim 11 wherein said porous fibrous sheet material is cotton cloth that is up to ~5 mm thick.

13. The structure of claim 1 wherein said sheet material consists essentially of cotton cloth.

14. The structure of claim 1 wherein said material is terry cloth.

15. The structure of claim 1 wherein said material is gauze.

16. The structure of claim 1 wherein said sheet material is cotton cloth that is up to ~5 mm thick.

17. The structure of claim 1 wherein said sheet material is sufficiently loosely convoluted to provide an average gap ranging from ~0.2 mm to 20 mm.

18. The structure of claim 1 wherein the direction of the fluid flow between said at least one inlet to said at least one outlet is substantially parallel to said gaps.

* * * * *

UNITED STATES PATENT AND TRADEMARK OFFICE
CERTIFICATE OF CORRECTION

PATENT NO. : 5,563,069
DATED : October 8, 1996
INVENTOR(S) : Yang

It is certified that error appears in the above-identified patent and that said Letters Patent is hereby corrected as shown below:

```
Column 7, line 17, change "congers" to --containers--.
Column 7, line 21, change "wig" to --within--. Column 11,
line 19, change "mines" to --amines--. Column 14, line 34,
change "I-IPLC" to --HPLC--. Column 15, line 67, change
"40 glacate" to -- 40 g lactate". Column 20, line 14,
change "outer" to --outlet--.
```

Signed and Sealed this

Tenth Day of December, 1996

Attest:

BRUCE LEHMAN

*Attesting Officer*  *Commissioner of Patents and Trademarks*